(12) United States Patent
Chanda et al.

(10) Patent No.: US 7,344,833 B2
(45) Date of Patent: Mar. 18, 2008

(54) METHODS AND COMPOSITIONS FOR MODULATING ACTIVATOR PROTEIN 1

(75) Inventors: Sumit Chanda, La Jolla, CA (US); Suhaila White, San Diego, CA (US); John B. Hogenesch, Encinitas, CA (US); Jeremy S. Caldwell, Cardiff, CA (US)

(73) Assignee: IRM LLC (BM)

( * ) Notice: Subject to any disclaimer, the term of this patent is extended or adjusted under 35 U.S.C. 154(b) by 547 days.

(21) Appl. No.: 10/702,112

(22) Filed: Nov. 5, 2003

(65) Prior Publication Data

US 2004/0146903 A1   Jul. 29, 2004

Related U.S. Application Data

(60) Provisional application No. 60/471,864, filed on May 20, 2003, provisional application No. 60/425,344, filed on Nov. 7, 2002.

(51) Int. Cl.
*C12Q 1/68* (2006.01)

(52) U.S. Cl. .......................................... 435/6; 435/7.1

(58) Field of Classification Search ..................... None
See application file for complete search history.

(56) References Cited

U.S. PATENT DOCUMENTS

| 5,989,908 | A | 11/1999 | Scanlon |
| 6,312,900 | B1 | 11/2001 | Dean et al. |
| 2003/0148954 | A1 | 8/2003 | Bresnick et al. |

FOREIGN PATENT DOCUMENTS

WO   WO2004/043370 A3   5/2004

OTHER PUBLICATIONS

PCT International Search Report mailed Jun. 16, 2004 for International Application No. PCT/US03/35367.
Malek SN, Dordai Di, Reim J, Dintzis H, Desiderio S. Related Articles, Links Malignant transformation of early lymphoid progenitors in mice expressing an activated Blk tyrosine kinase. Proc Natl Acad Sci U S A. Jun. 23, 1998;95(13):7351-6.
Kyriakis J. Activation of the AP-1 Transcription Factor by Inflamatory Cytokines of the TNF Family. Gene Expression. 1999, vol. 7, pp. 217-213.
Pyrzynska B. et al. Changes of the Trans Activating Potential of AP-1 Transcription Factor During Cyctosporin A Induced Apoptosis of Clioma Cells Are Mediated by Phosphorylation and Alterations of AP-1 Composition. Journal of Neurochemistry. 2000, vol. 74, pp. 42-51.
Ozolins et al. Post-Translational Regulation of AP-1 Transcription Factor DNA Binding Activity in the Rat Conceptus. Molecular Pharmacology. 1999, vol. 56, No. 3, pp. 537-544.
BD Biosciences Clontech—Technical Info: pAP1 (PMA)- TA-Luc Vector. www.clonetech.com/techinfo/vectors/vectorsA-B/pAP1(PMA)- TA-Luc.shtml. 1 page, Accessed Jul. 25, 2001.
Acive Motif: TransAM AP-1. www.activemotif.com/products/cell/transam/ap1.html. 2 pages, Accessed Oct. 17, 2002.
Wisdom, Ron. AP-1: One Switch for Many Signals. Experimental Cell Research. 1999. vol. 253, pp. 80-185.

*Primary Examiner*—James Ketter
(74) *Attorney, Agent, or Firm*—Timothy L. Smith; Genomics Institute of the Novartis Research Foundation

(57) ABSTRACT

This invention provides novel AP-1 modulatory polypeptides. The invention also provides methods for screening modulators of AP-1 transcription factor activities. The methods comprise first screening test agents for modulators of an AP-1-modulatory polypeptide and then further screening the identified modulating agents for modulators of AP-1 transcription factor activities. The invention further provides methods and pharmaceutical compositions for modulating AP-1 transcription factor activities in a cell and for treating diseases and conditions mediated by abnormal cellular proliferation.

18 Claims, 3 Drawing Sheets

METHODS AND COMPOSITIONS FOR MODULATING ACTIVATOR PROTEIN 1

CROSS-REFERENCE TO RELATED APPLICATIONS

Figure 1:
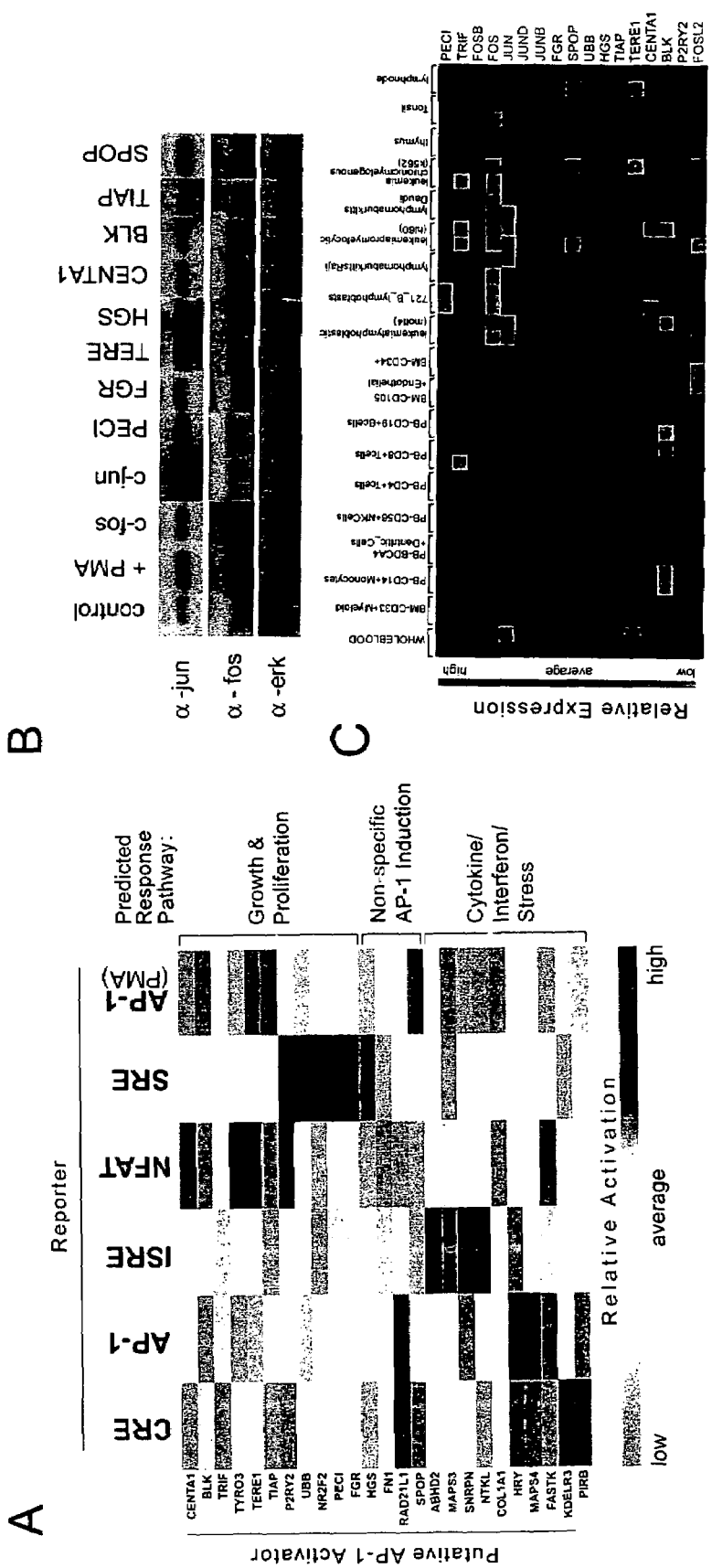

This application claims the benefit of priority to U.S. Provisional Patent Application Ser. Nos. 60/425,344 (filed Nov. 7, 2002) and 60/471,864 (filed May 20, 2003). The full disclosures of these applications are incorporated herein by reference in their entirety and for all purposes.

FIELD OF THE INVENTION

The present invention generally relates to methods for identifying modulators of activator protein 1 and therapeutic applications of such modulators. More particularly, the invention pertains to novel AP-1 modulators that regulate transcription factor activities and cellular levels of AP-1 or AP-1 subunits, and to methods of using such modulators to modulate AP-1 transcription factor activities or cellular levels in a subject.

BACKGROUND OF THE INVENTION

Transcription factors play a central role in the expression of specific genes upon stimulation by extracellular signals, thereby regulating a complex array of biological processes. Activator protein 1 (AP-1), also termed "activating protein 1," "activation protein 1," or "AP-1 transcription factor," is a heterogenous mixture of heterodimers of several related protein subunits (Kodonaga and Tijan, Proc. Natl. Acad. Sci. USA, 83, 5889-5893, 1986). One notable member of the AP-1 family is the heterodimer formed of c-Fos and c-Jun. These two proteins are products of the c-fos and c-jun proto-oncogenes, respectively. Other subunits of AP-1 family include FosB, Fra-1, Fra-2, c-Jun, JunB, JunD, etc. (see, e.g., *The FOS and JUN Families of Proteins*, Angel and Herrlich, eds., CRC Press, Boca Raton, Fla., 1994; and SteinmÄller et al., Biochem J, 360: 599-607, 2001).

AP-1 has been implicated in abnormal cell proliferation and tumor formation. Members of AP-1 family alter gene expression in response to growth factors, cytokines, tumor promoters, carcinogens and increased expression of certain oncogenes. AP-1 proteins are expressed by lymphoid cells, and bind to effector cells such as macrophages and mast cells. In particular, the AP-1 proteins induce macrophage phagocytosis, expression of class II major histocompatibility molecules, cytotoxicity, and migration, and induce hematopoietic progenitor cell differentiation.

Modulation of AP-1 transcription factor activities or cellular levels would affect various cellular processes and provide therapeutic means for treating a number of diseases and conditions. There is a need in the art for novel methods and compositions for modulating AP-1 transcription factor activities and thereby inhibiting cell proliferation in tumor formation and tumor growth. The instant invention fulfills this and other needs.

SUMMARY OF THE INVENTION

The present invention relates to novel AP-1-modulatory polypeptides, methods for screening modulators of AP-1 transcription factor, and methods for modulating AP-1 transcription factor activities in a cell. In one aspect, the invention provides methods for identifying agents that modulate activities of AP-1 transcription factor. The methods comprise (i) assaying a biological activity of an AP-1-modulatory polypeptide of the present invention or its fragment in the presence of test agents, and identifying modulating agents that modulate the biological activity of the polypeptide; and (ii) testing the modulating agents for ability to modulate an AP-1 transcription factor.

In some of the methods, the modulating agents identified are tested for ability to modulate an AP-1 transcription factor activity in regulating expression of an AP-1 responsive gene. In some of the methods, the modulating agents identified are tested for ability to modulate cellular level of the AP-1 transcription factor or a subunit of the AP-1 transcription factor. The AP-1 subunit tested in these methods can be selected from the group consisting of c-Fos, FosB, Fra-1, Fra-2, c-Jun, JunB and JunD. 22.

In some methods, the AP-1-modulatory polypeptide is selected from the group consisting of CENTA 1, TIAP, BLK, and TYRO3. In some methods, the AP-1-modulatory polypeptide employed is a kinase and the biological activity assayed is phosphorylation of a second polypeptide. In other methods, the AP-1-modulatory polypeptide is a protease and the biological activity is proteolysis of a second polypeptide. The second polypeptide used in these methods can be a subunit of AP-1 transcription factor.

In some methods, the test agents modulate cellular level of the AP-1-modulatory polypeptide. In some methods, assaying of the biological activity of the AP-1-modulatory polypeptide occurs in a cell. In some of the latter methods, the AP-1-modulatory polypeptide is expressed from a polynucleotide that has been introduced into the cell.

In some methods, the AP-1 transcription factor activity is inducing expression of a second polynucleotide that is operably linked to an AP-1 response element. The second polynucleotide can encode a reporter polypeptide. In some of these methods, the testing for ability to modulate an AP-1 transcription factor activity comprises (i) providing a cell or cell lysate that comprises the second polynucleotide that is operably linked to the AP-1 response element; (ii) contacting the cell or cell lysate with the test agent; and (iii) detecting an increase or decrease in expression of the second polynucleotide in the presence of the test agent compared to expression of the second polynucleotide in the absence of the test agent.

In other methods, the testing for ability to modulate an AP-1 transcription factor activity comprises contacting a cell or cell lysate with the test agent and determining cellular level of the AP-1 transcription factor or a subunit of the AP-1 transcription factor. In other methods, the testing for ability to modulate the AP-1 transcription factor activity comprises contacting a cell or cell lysate with the test agent and determining ability of the AP-1 transcription factor to bind to a second polynucleotide that comprises an AP-1 response element in the cell or cell lysate. The AP-1 transcription factor employed in these methods can be, e.g., a Jun/Fos heterodimer.

In one aspect, the invention provides methods for identifying agents that modulate cellular level of an AP-1 transcription factor or a subunit of the AP-1 transcription factor. These methods comprise (i) assaying a biological activity of an AP-1-modulatory polypeptide of the present invention, or a fragment of the polypeptide, in the presence of a test agent to identify a modulating agent that modulates the biological activity of the polypeptide; and (ii) testing the modulating agent for ability to modulate the cellular level of the AP-1 transcription factor or a subunit of the AP-1 transcription factor.

In some of the methods, the AP-1-modulatory polypeptide is a transcription regulatory protein and the biological activity is transcription of a second polynucleotide. In some of these methods, the testing comprises (i) contacting the modulating agent with a second polynucleotide operably linked to a transcription regulatory element of an AP-1 subunit; and (ii) detecting a change in cellular level of the second polynucleotide relative to cellular level of the second polynucleotide in the absence of the modulating agent. In some of the methods, the contacting occurs in a cell. In some of the methods, the second polynucleotide encodes a reporter polypeptide. In some of the methods, the second polynucleotide encodes an AP-1 subunit. The AP-1 subunit can be selected from the group consisting of c-Fos, FosB, Fra-1, Fra-2, c-Jun, JunB and JunD.

In one aspect, the invention provides methods for identifying agents that modulate expression of an AP-1 responsive gene. These methods comprise (i) contacting a test agent with an AP-1-modulatory polypeptide; (ii) detecting a change in an activity of the AP-1-modulatory polypeptide relative to the activity in the absence of the test agent; and (iii) detecting a change of expression level of the AP-1 responsive gene in the presence of the test agent identified in (ii) relative to expression level of the AP-1 responsive gene in the absence of the test agent; thus identifying the test agent as a modulator of expression of the AP-1 responsive gene.

In another aspect, the subject invention provides methods for modulating an AP-1 transcription factor activity in a cell. These methods comprise administering to the cell an effective amount of an AP-1 modulatory polypeptide or a fragment of the AP-1 modulatory polypeptide, thus modulating the AP-1 transcription factor activity. In some of these methods, the AP-1 modulatory polypeptide or its fragment is expressed from an expression vector that has been introduced into the cell. In some methods, the modulating is increasing cellular level of the AP-1 transcription factor.

In another aspect, the invention provides methods for modulating an AP-1 transcription factor activity in a cell. The methods comprise administering to the cell an effective amount of an AP-1 modulator identified in accordance with the present invention, thereby modulating the AP-1 transcription factor activity. In some of these methods, the modulating is increasing cellular level of the AP-1 transcription factor.

BRIEF DESCRIPTION OF THE DRWAINGS

FIGS. 1A-1C show functional validation of AP-1 modulators. (A) The activities of 25 activators of AP-1 (PMA) signaling were profiled in triplicate against AP-1-related reporter constructs sensitive to growth and proliferation stimuli (AP-1 (PMA), SRE, and NFAT (plus ionomycin)), and stress/cytokine induction (CRE, AP-1, ISRE). To account for differential dynamic range inherent to each response element, reporter (columns) and gene (rows) activities were normalized and clustered using a hierarchical algorithm. Predicted response pathways are based on clustered gene activities upon a subset of reporter constructs, and previously unannotated genes are indicated in blue text; (B) Induction of endogenous c-FOS and c-JUN protein levels by transfection of "growth" and "non-specific" responsive subset of indicated AP-1 modulators into HEK293 cells was assessed through western blot analysis. Cell lysate from parental vector (pCMVSport6) transfected HEK293 cells were used as a negative control, and c-FOS and c-JUN transfected and PMA-treated cell extracts were utilized as positive controls. Levels of ERK1 and ERK2 were detected to control for loading; (C) Co-expression based upon microarray analysis of canonical and identified AP-1 pathway members in primarily lymphoid cell types are shown. Relative mRNA levels shown were derived from comparison to over 50 random primary tissue and cell types.

Figure 2:
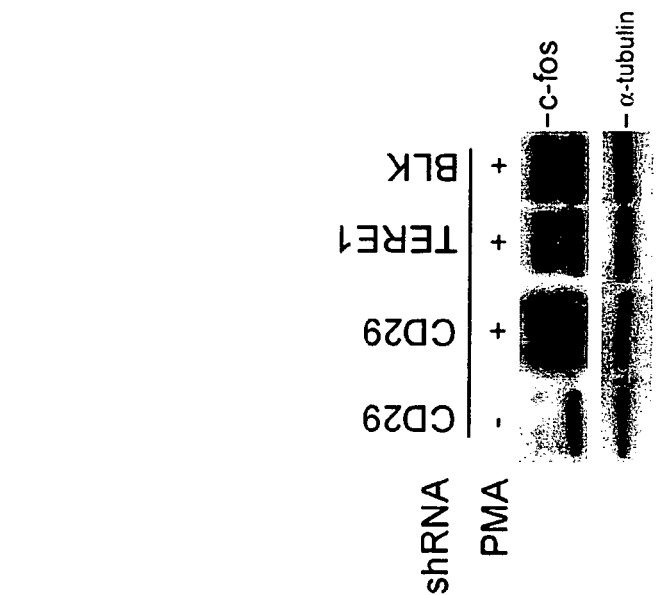
Figure 2:
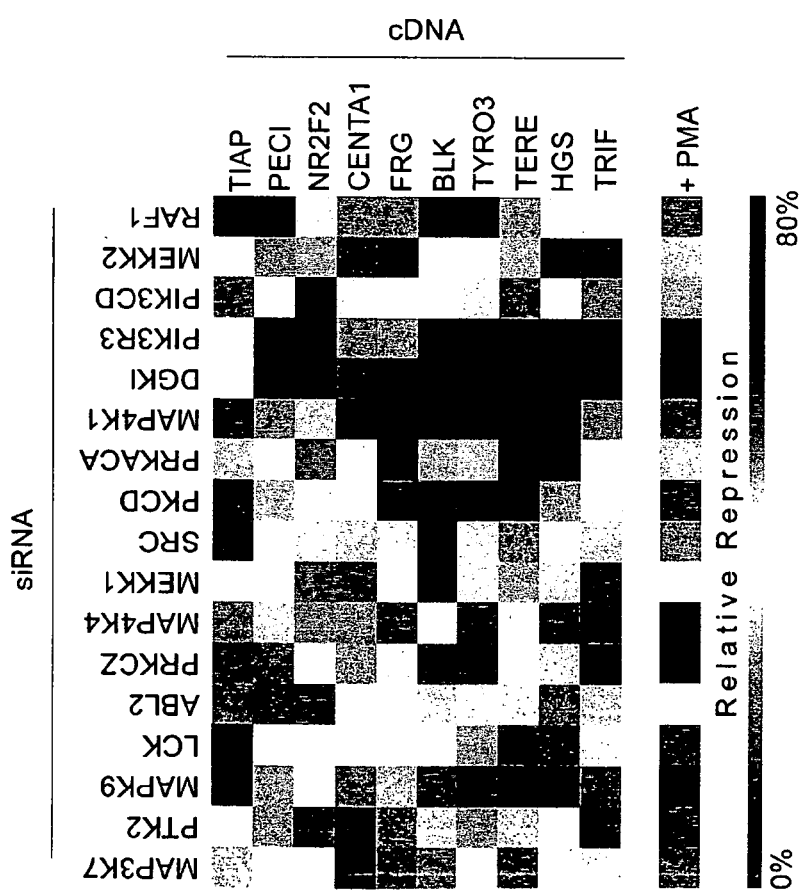

FIGS. 2A-2B show siRNA-mediated functional mapping of AP-1 growth effectors. (A) HEK293 cells were transfected with indicated siRNAs (columns), and subsequently transfected in a pairwise manner with indicated cDNAs (rows), along with an AP-1 (PMA) dependent luciferase reporter construct and a constitutive β-galactosidase reporter vector. After 48 hours of incubation, fractional luciferase/β-galatosidase values were determined for each well and further normalized to the activities of three non-specific siRNA control wells for each transfected cDNA. The resulting data was analyzed utilizing hierarchical clustering and visualized in Treeview (Stanford University), and depicted the average of at least three experiments. Effects of siRNA molecules upon PMA stimulated AP-1 activity is also shown; (B) Short-hairpin RNAs (shRNAs) targeting predicted growth and proliferation modulators TERE1 and BLK, and a non-specific control (CD29), were transfected into HEK293 cells. Cultures were treated with PMA for 24 hours as indicated, and cell lysates were interrogated for c-FOS induction through western blot analysis. Levels of alpha-tubulin protein were also detected to serve as loading controls.

Figure 3:
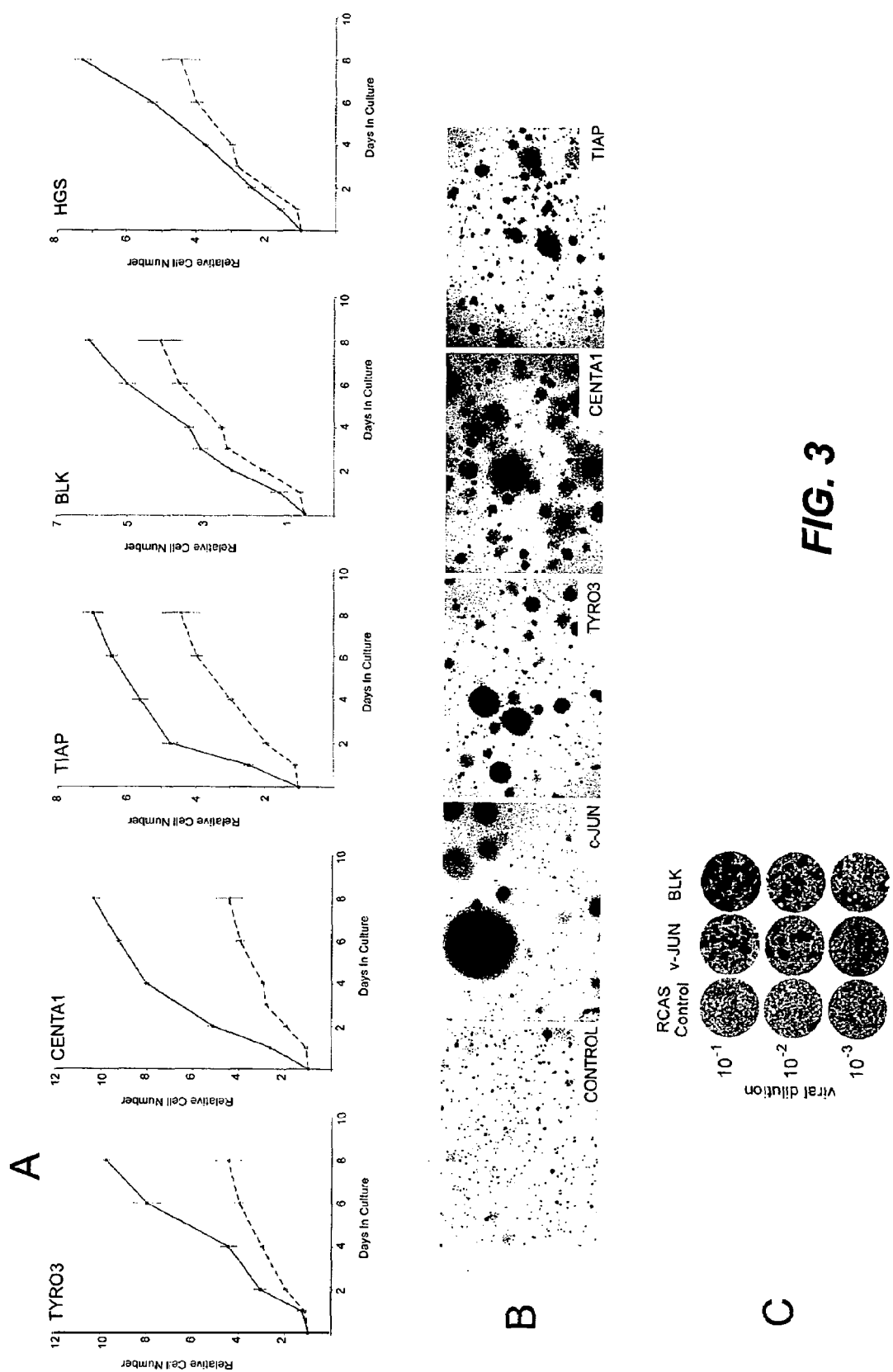

FIGS. 3A-3C show identification of candidate oncogenes associated with AP-1 proliferation. (A) Predicted modulators of AP-1 mediated proliferation are subcloned into the RCAS retroviral expression system (26), and transfected into primary Chicken Embryonic Fibroblast cells (CEFs). Viral supernatants were transferred to fresh CEFs. Cells were then plated at a density of approximately 5×10 5 in 6 well plates and cell counts were initially taken after 24 hours (day 0) and at the indicated time points. Ectopically expressed genes (solid line) are indicated on each graph and compared to RCAS only control (dashed line). Results are shown as the function of initial seeding density (day 0) and depict the average of 3 experiments; (B) CEF cells were infected with retroviruses encoding c-JUN, TYRO3, CENTA1, TIAP, and RCAS control. Cells were maintained in soft agar for 4 weeks. Colony formation was assessed by visual inspection; (C) CEF cells infected with BLK, c-JUN, or control RCAS retroviruses, and 24 hours post infection the cells were overlayed with agar medium and maintained in culture for 10 to 14 days. Foci were visualized by crystal violet staining.

DETAILED DESCRIPTION

The invention is predicated in part on the discovery by the present inventors of novel modulators of AP-1 signaling pathways. In accordance with the discovery, the present invention provides methods for identifying modulators of AP-1 transcription factor and novel AP-1 modulators. The invention also provides methods for modulating AP-1 transcription factor in a cell and for treating diseases or conditions mediated by abnormal activities or cellular levels of AP-1 transcription factor. The following sections provide guidance for making and using the compositions of the invention, and for carrying out the methods of the invention.

I. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). In addition, the following definitions are provided to assist the reader in the practice of the invention.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

As used herein, "contacting" has its normal meaning and refers to combining two or more agents (e.g., two polypeptides) or combining agents and cells (e.g., a protein and a cell). Contacting can occur in vitro, e.g., combining two or more agents or combining a test agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

A "heterologous sequence" or a "heterologous nucleic acid," as used herein, is one that originates from a source foreign to the particular host cell, or, if from the same source, is modified from its original form. Thus, a heterologous gene in a host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "homologous" when referring to proteins and/or protein sequences indicates that they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and/or the like.

The terms "identical", "sequence identical" or "sequence identity" in the context of two nucleic acid sequences or amino acid sequences refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman (1981) Adv. Appl. Math. 2:482; by the alignment algorithm of Needleman and Wunsch (1970) J. Mol. Biol. 48:443; by the search for similarity method of Pearson and Lipman (1988) Proc. Nat. Acad. Sci U.S.A. 85:2444; by computerized implementations of these algorithms (including, but not limited to CLUSTAL in the PC/Gene program by Intelligentics, Mountain View, Calif.; and GAP, BESTFIT, BLAST, FASTA, or TFASTA in the Wisconsin Genetics Software Package, Genetics Computer Group (GCG), 575 Science Dr., Madison, Wis., U.S.A.). The CLUSTAL program is well described by Higgins and Sharp (1988) Gene 73:237-244; Higgins and Sharp (1989) CABIOS 5:151-153; Corpet et al. (1988) Nucleic Acids Res. 16:10881-10890; Huang et al (1992) Computer Applications in the Biosciences 8:155-165; and Pearson et al. (1994) Methods in Molecular Biology 24:307-331. Alignment is also often performed by inspection and manual alignment. In one class of embodiments, the polypeptides herein are at least 70%, generally at least 75%, optionally at least 80%, 85%, 90%, 95% or 99% or more identical to a reference polypeptide, e.g., an AP-1-modulatory polypeptide encoded by a polynucleotide in Table 1 or 2, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 95%, 99% or more identical to a reference nucleic acid, e.g., as measured by BLASTN (or CLUSTAL, or any other available alignment software) using default parameters.

The terms "substantially identical" nucleic acid or amino acid sequences means that a nucleic acid or amino acid sequence comprises a sequence that has at least 90% sequence identity or more, preferably at least 95%, more preferably at least 98% and most preferably at least 99%, compared to a reference sequence using the programs described above (preferably BLAST) using standard parameters. For example, the BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

The term "isolated" means that the material is removed from its original environment (e.g., the natural environment if it is naturally occurring). For example, a naturally-occurring nucleic acid, polypeptide, or cell present in a living animal is not isolated, but the same polynucleotide, polypeptide, or cell separated from some or all of the coexisting materials in the natural system, is isolated, even if subsequently reintroduced into the natural system. Such nucleic acids can be part of a vector and/or such nucleic acids or polypeptides could be part of a composition, and still be isolated in that such vector or composition is not part of its natural environment.

The terms "nucleic acid," "DNA sequence" or "polynucleotide" refer to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. A "polynucleotide sequence" is a nucleic acid (which is a polymer of nucleotides (A,C,T,U,G, etc. or naturally occurring or artificial nucleotide analogues) or a character string representing a nucleic acid, depending on context. Either the given nucleic acid or the complementary nucleic acid can be determined from any specified polynucleotide sequence.

The term "modulate" with respect to an AP-1 transcription factor refers to a change in the cellular level or other biological activities of the AP-1 transcription factor complex or its subunits (e.g., Jun or Fos). For example, modulation may cause an increase or a decrease in cellular levels of AP-1 or its subunits, enzymatic modification (e.g., phosphorylation) of AP-1 or its subunits, binding characteristics (e.g., binding to a target transcription regulatory element), or any other biological, functional, or immunological properties of such proteins. The change in activity can arise from, for example, an increase or decrease in expression of one or more genes that encode AP-1 subunits, the stability of an mRNA that encodes the AP-1 subunits, translation efficiency, or from a change in activity of the AP-1 transcription factor complex (or a subunit) itself. The change can also due to the activity of another molecule that modulates AP-1 or its subunits (e.g., a kinase which phosphorylates the Jun subunit).

Modulation of AP-1 activities can be up-regulation (i.e., activation or stimulation) or down-regulation (i.e. inhibition or suppression). The mode of action of an AP-1 modulator can be direct, e.g., through binding to AP-1 or to genes encoding AP-1 subunits (e.g., fos or jun), or indirect, e.g., through binding to and/or modifying (e.g., enzymatically) another molecule which otherwise modulates AP-1 (e.g., a kinase which specifically phosphorylates a AP-1 subunit).

The term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The term "operably linked" refers to a functional relationship between two or more polynucleotide (e.g., DNA) segments. Typically, it refers to the functional relationship of a transcriptional regulatory sequence to a transcribed sequence. For example, an AP-1 promoter or enhancer sequence, is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance. A polylinker provides a convenient location for inserting coding sequences so the genes are operably linked to the AP-1 promoter. Polylinkers are polynucleotide sequences that comprise a series of three or more closely spaced restriction endonuclease recognition sequences.

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "polypeptide" is used interchangeably herein with the terms "polypeptides" and "protein(s)", and refers to a polymer of amino acid residues, e.g., as typically found in proteins in nature. A "mature protein" is a protein which is full-length and which, optionally, includes glycosylation or other modifications typical for the protein in a given cell membrane.

The promoter region of a gene includes the transcription regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product. The promoter region may be a normal cellular promoter or an oncopromoter.

The term "recombinant" has the usual meaning in the art, and refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. When used with reference to a cell, the term indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of affecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed and a promoter. Additional factors necessary or helpful in effecting expression can also be used as described herein. For example, transcription termination signals, enhancers, and other nucleic acid sequences that influence gene expression, can also be included in an expression cassette.

Transcription refers to the process involving the interaction of an RNA polymerase with a gene, which directs the expression as RNA of the structural information present in the coding sequences of the gene. The process includes, but is not limited to the following steps: (1) transcription initiation, (2) transcript elongation, (3) transcript splicing, (4) transcript capping, (5) transcript termination, (6) transcript polyadenylation, (7) nuclear export of the transcript, (8) transcript editing, and (9) stabilizing the transcript.

A transcription regulatory element or sequence include, but is not limited to, a promoter sequence (e.g., the TATA box), an enhancer element, a signal sequence, or an array of transcription factor binding sites. It controls or regulates transcription of a gene operably linked to it.

A "variant" of a molecule such as a modulator of AP-1 is meant to refer to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

A "vector" is a composition for facilitating introduction, replication and/or expression of a selected nucleic acid in a cell. Vectors include, e.g., plasmids, cosmids, viruses, YACs, bacteria, poly-lysine, etc. A "vector nucleic acid" is a nucleic acid molecule into which heterologous nucleic acid is optionally inserted which can then be introduced into an appropriate host cell. Vectors preferably have one or more origins of replication, and one or more sites into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes." "Expression vectors" are vectors that comprise elements that provide for or facilitate transcription of nucleic acids that are cloned into the vectors. Such elements can include, e.g., promoters and/or enhancers operably coupled to a nucleic acid of interest.

II. Identification of Novel AP-1-Modulatory Polypeptides

As used in the present invention, the consensus binding sites on a target gene that is regulated by an AP-1 transcription factor (i.e., an AP-1 responsive gene) are interchangeably termed "AP-1 recognition sequences," "AP-1 response elements," "AP-1 binding sites," or "TPA-responsive elements (TREs)." These enhancer sequences are found in many AP-1 responsive genes and usually have a consensus sequence of TGAGTCA, TGACTCA, TGACTAA, or TGACGCA (see, Hirai et al., New Biol. 1: 181-91, 1989; Thierry et al., J. Virol. 66: 3740-8, 1992; and Sassone-Corsi et al., Cell 54: 553-60, 1988). In addition to AP-1, a few other regulatory proteins are also known to bind to the same or similar sequences as these enhancer elements. Example of genes containing the AP-1-binding enhancer sequences have been described in the art, e.g., as described in U.S. Pat. No. 5,989,908; Ransone et al., Ann. Rev. Cell Biol. 6:539-557, 1990; Ransone et al., Int. J. Cancer Supplement 4:10-21, 1989; and Kouzarides et al., Cancer Cells 1:71-76, 1989.

AP-1 binding sites are also present in genes encoding AP-1 subunits (e.g., jun and fos). Other than trans-regulating expression of AP-1 responsive genes under its control, the AP-1 transcription factor also auto-regulates expression of its own subunits. For example, AP-1 can bind to AP-1 recognition sequences on genes encoding AP-1 subunits (e.g., Jon or Fos; see, e.g., Sassone-Corsi, Nature 334:314-319, 1988; Hata et al., IUBMB Life, 49: 229-34, 2000).

The present invention provides novel protein or polypeptide modulators that modulate AP-1 transcription factor activities. Utilizing an expression vector which expresses a reporter gene under the control of six tandem repeats of an AP-1 responsive sequence, a number of polynucleotides were identified which up-regulate expression of the reporter gene when the expression vector and the polynucleotides were co-transfected into a host cell (see, Example 1). An exemplary list of polynucleotides encoding such AP-1-modulatory polypeptides that were identified in accordance with the present invention is shown in Tables 1 and 2. As shown in the Table, the novel AP-1-modulatory polypeptides include very diversified classes of proteins, including kinases, phosphatases, receptor polypeptides, phosphatidylinositol binding protein, and etc.

As noted above, the AP-1 transcription factor also auto-regulates expression of AP-1 subunits, and AP-1 response elements are also present in genes encoding AP-1 subunits (e.g., jun or fos). Therefore, the up-regulation of reporter gene expression by the AP-1 modulatory polypeptides shown in Tables 1 and 2 could be due to a direct effect on the AP-1 responsive element in the expression construct and transcription of the reporter gene. Alternatively, the up-regulation could also be the result of enhanced expression or activity of endogenous AP-1 that in turn modulates expression of the reporter gene.

Thus, the AP-1-modulatory polypeptides identified by the present inventors can operate with a number of mechanisms in modulating AP-1 transcription factor activities. They can modulate upstream pathways leading to AP-1 activation (e.g., a kinase). AP-1 is activated by and respond to very diversified signals, e.g., cellular stress, ionizing and ultraviolet irradiation, DNA damage, oxidative stress, neuronal depolarization, antigen binding by T or B lymphocytes, cytoskeletal rearrangements, and cytokines such as tumor necrosis factor-α and interferon-γ (see, e.g., Wisdom, Exp. Cell Res. 253: 180-185, 1999). For example, the AP-1-modulatory polypeptides can stimulate AP-1 function by modulating growth factor signaling pathways (see, e.g., Kyriakis et al., Gene Expr. 7: 217-31, 1999).

The AP-1-modulatory polypeptides could also exert regulatory function on expression of AP-1 subunits and cellular activities of an AP-1 transcription factor. They can stimulate expression of AP-subunits or otherwise increase cellular activities of AP-1 by, e.g., modulating events relating to transcription of a gene encoding an AP-1 subunit, modulating post-transcriptional processing, modulating translation of AP-1 subunits, modulating post-translational modification, modulating assembly of an AP-1 heterodimer, or modulating stability or proteolysis of AP-1 complex or its subunits. The AP-1-modulatory polypeptides can also act by modulating other biological activities of the AP-1 transcription factor that are necessary for or involved in the transcription regulating function of AP-1 (e.g., modulating phosphorylation of AP-1 subunits or DNA-binding activity of AP-1). For example, phosphorylation of AP-1 subunits plays an important role in regulating AP-1 cellular activity. Mitogen-activated protein (MAP) kinases, Jun kinase 1 and Jun kinase 2, are responsible for the phosphorylation of specific sites (Serine 63 and Serine 73) on c-Jun. Phosphorylation of these sites potentiates the ability of AP-1 to activate transcription (Binetruy et al., Nature 351: 122, 1991; Smeal et al., Nature, 1991, 354, 494; and Pyrzynska et al., J. Neurochem. 74: 42-51, 2000).

III. Methods for Screening Modulators of AP-1 Transcription Factor Activities The AP-1-modulatory polypeptides described above provide novel targets for screening modulators (agonists or antagonists) of the AP-1 transcription factor activities. The novel AP-1 modulators can be used to modulate transcription regulation of AP-1 responsive genes. The expression of an AP-1 responsive gene can be positively or negatively regulated to provide, respectively, for increased or decreased production of the protein whose expression is mediated by AP-1 recognition sequence. Furthermore, genes, which do not, in their wild type form, have AP-1 recognition sequences, can be placed under the control of AP-1 by inserting an AP-1 binding site in an appropriate position, using techniques known to those skilled in the art. Thus, expression of such genes can also be modulated by AP-1 modulators of the present invention.

A. General Scheme and Assay Systems

Employing the novel AP-1-modulatory polypeptides described above, the present invention provides methods for screening agents or compounds that modulate activities of an AP-1 transcription factor. Various biochemical and molecular biology techniques or assays well known in the art can be employed to practice the present invention. Such techniques are described in, e.g., Sambrook et al., *Molecular Cloning: A Laboratory Manual*, Cold Spring Harbor Press, N.Y., Second (1989) and Third (2000) Editions; and Ausubel et al., *Current Protocols in Molecular Biology*, John Wiley & Sons, Inc., New York (1987-1999).

In some methods, test agents are first assayed for their ability to modulate a biological activity of an AP-1-modulatory polypeptide ("the first assay step"). Modulating agents thus identified are then subject to further screening for ability to modulate an activity of the AP-1 transcription factor, typically in the presence of the AP-1-modulatory polypeptide ("the second testing step"). Depending on the AP-1-modulatory polypeptide employed in the method, modulation of different biological activities of the AP-1-modulatory polypeptide can be assayed in the first step. For example, a test agent can be assayed for binding to the AP-1-modulatory polypeptide. The test agent can be assayed for activity to modulate expression level of the AP-1-modulatory polypeptide, e.g., transcription or translation. The test agent can also be assayed for activities in modulating cellular level or stability of the AP-1-modulatory polypeptide, e.g., post-translational modification or proteolysis.

If the AP-1-modulatory polypeptide has a known or well established biological or enzymatic function (e.g., kinase activity, protease activity, or DNA-binding activity), the biological activity monitored in the first screening step can be the specific biochemical or enzymatic activity of the AP-1-modulatory polypeptide. For example, kinase activity of TYRO3 or BLK, or trisphosphate binding activity of CENTA1, can be monitored in the first screening step if any of these AP-1 modulator is employed in the screening. In an exemplary embodiment, the AP-1-modulatory polypeptide is a kinase (e.g., encoded by Accession No. NM_033015.1, XM_034315.1, XM_166235.1, or NM_006293), and test agents are first screened for modulating the kinase's activity in phosphorylating a substrate. The substrate can be a polypeptide known to be phosphorylated by the kinase. The substrate can also be an AP-1 transcription factor, an AP-1 subunit, or a fragment thereof. For example, as disclosed in the Examples below, BLK forms complex with chaperon CDC37 as demonstrated by immunoprecipitation. Therefore, the substrate used in the assay can be CDC37.

TABLE 1

Polynucleotides encoding novel AP-1-modulatory polypeptides

| | GenBank Acc. No. | Description of the polynucleotide sequence and encoded polypeptide | Fold of modulation |
|---|---|---|---|
| 1 | NM_012216 | 012216 *Homo sapiens* midline 2 (MID2), transcript variant 1 | 9.15 x |
| 2 | AF082324 | *Homo sapiens* phosphatidylinositol (3,4,5) trisphosphate binding protein (CENTA1) | 32.1 x |
| 3 | AK021623 | *Homo sapiens* cDNA FLJ11561 fis, clone HEMBA1003142 | 9.35 x |
| 4 | AK027878.1 | *Homo sapiens* cDNA FLJ14972 fis, clone THYRO1000715; also termed KIAA1847 ("TIAP") | 3.65 x |
| 5 | AK056412 | *Homo sapiens* cDNA FLJ31850 fis, clone NT2RP7000600; highly similar to *Homo sapiens* activating receptor PILRbeta | |
| 6 | AK074258.1 | *Homo sapiens* cDNA FLJ23678 fis, clone HEP08720 | |
| 7 | AJ228839.1 | *Homo sapiens* ITGA7 gene, exon 4 | |

TABLE 1-continued

Polynucleotides encoding novel AP-1-modulatory polypeptides

| | GenBank Acc. No. | Description of the polynucleotide sequence and encoded polypeptide | Fold of modulation |
|---|---|---|---|
| 8 | X74104.1 | *H. sapiens* mRNA for TRAP beta subunit; encoding beta subunit of the human translocon-associated protein | |
| 9 | AC006318.2 | AC006318 *Homo sapiens* clone RP4-728I19 | |
| 10 | AC008243 | *Homo sapiens*, clone RP11-45L9 | |
| 11 | AF090916 | *Homo sapiens* clone HQ0312 | |
| 12 | AF110821 | *Homo sapiens* glucose-6-phosphate translocase | 4 x |
| 13 | AF173157 | *Homo sapiens* MSTP098 (MST098) | |
| 14 | AF277374 | *Homo sapiens* enhancer of polycomb | |
| 15 | AF461760.1 | *Homo sapiens* zinc transporter 5 (ZNT5) | |
| 16 | BC001269 | *Homo sapiens*, speckle-type POZ protein, clone MGC: 5068 | 77.6 x |
| 17 | BC001277 | *Homo sapiens*, KDEL (Lys-Asp-Glu-Leu) endoplasmic reticulum protein retention receptor 3, clone MGC: 5099 | |
| 18 | BC003565 | *Homo sapiens*, hepatocyte growth factor-regulated tyrosine kinase substrate, clone MGC: 2045 | 54 x |
| 19 | BC012718 | BC012718 *Mus musculus*, Similar to glucagon receptor | |
| 20 | BC014664 | *Homo sapiens*, nuclear receptor subfamily 2, group F, member 2, clone MGC: 23125 | 149.8 x |
| 21 | BC016863 | *Homo sapiens*, Similar to sorting nexin 3, clone MGC: 17570 | |
| 22 | BC016958 | *Homo sapiens*, hypothetical protein DKFZp761H1710, clone MGC: 21544 | |
| 23 | BC017168 | *Homo sapiens*, clone MGC: 9517 | 3.65 x |
| 24 | BC018708 | *Homo sapiens*, hypothetical protein FLJ14451, clone MGC: 31767 | |
| 25 | BC022023 | *Homo sapiens*, Similar to hypothetical protein DKFZp434A171 | |
| 26 | BC025178.1 | *Homo sapiens*, small nuclear ribonucleoprotein polypeptide N, clone MGC: 34180 | |
| 27 | BC028135.1 | *Homo sapiens*, purinergic receptor P2Y, G-protein coupled, 2, clone MGC: 40010 | 85.2 x |
| 28 | NM_018955 | *Homo sapiens*, clone MGC: 32826 (*Homo sapiens* ubiquitin B, UBB) | |
| 29 | BC031027.1 | *Homo sapiens*, clone MGC: 32826 | 28.3 x |
| 30 | NM_002896.1 | *Homo sapiens* RNA binding motif protein 4 (RBM4) | |
| 31 | NM_006117.1 | *Homo sapiens* peroxisomal D3,D2-enoyl-CoA isomerase (PECI) | 66.3 x |
| 32 | NM_013319.1 | *Homo sapiens* transitional epithelia response protein (TERE1) | 39.65 x |
| 33 | NM_031209.1 | *Homo sapiens* tRNA-guanine transglycosylase (TGT) | |
| 34 | NM_033015.1 | *Homo sapiens* FAST kinase (FASTK) transcript variant 2 | 8.9 x |
| 35 | NM_052972.1 | *Homo sapiens* leucine-rich alpha-2-glycoprotein (LRG) | 3.95 x |
| 36 | XM_002279.6 | *Homo sapiens* inositol polyphosphate-1-phosphatase (INPP1) | |
| 37 | XM_011695.6 | *Homo sapiens* leptin receptor overlapping transcript-like 1 (LEPROTL1) | |
| 38 | XM_031536.2 | *Homo sapiens* hypothetical protein (MAC30) | 25.1 x |
| 39 | XM_034315.1 | *Homo sapiens* B lymphoid tyrosine kinase (BLK) | 35 x |
| 40 | XM_035634.2 | *Homo sapiens* hypothetical protein, clone 24751 (CL24751) | 75.25 x |
| 41 | XM_035662.2 | *Homo sapiens* cathepsin B (CTSB) | |
| 42 | XM_039925.4 | *Homo sapiens* hairy homolog (Drosophila) (HRY) | 29.5 x |
| 43 | XM_042224.2 | *Homo sapiens* hypothetical protein FLJ11151 (FLJ11151) | |
| 44 | XM_166235.1 | *Homo sapiens* N-terminal kinase-like (NTKL) | 7.15 x |
| 45 | XM_092768 | *Homo sapiens* similar to dJ545L17.2 (novel protein similar to RAD21 (S. pombe) homolog (KIAA0078)) (LOC164298) | 5.4 x |
| 46 | NM_007011 | *Homo sapiens* abhydrolase domain containing 2 (ABHD2), transcript variant 1 | 12 x |
| 47 | NM_003097 | *Homo sapiens* small nuclear ribonucleoprotein polypeptide N (SNRPN) | 12 x |

TABLE 2

Additional AP-1-modulators

| | MGC11k.GenBank | Symbol | Annotation | Fold of modulation |
|---|---|---|---|---|
| 48 | BC032229 | AXL | | 71.2 |
| 49 | BC027849 | GRP3 | guanine nucleotide exchange factor for Rap1 | 12.9 |
| 50 | BC030878 | 0610009B10Rik | RIKEN cDNA 0610009B10 gene | 19.1 |
| 51 | BC025695 | EDG4 | endothelial differentiation, lysophosphatidic acid G-protein-coupled receptor, 4 | 12.3 |
| 52 | BC027331 | | | 18.3 |

TABLE 2-continued

Additional AP-1-modulators

| | MGC11k.GenBank | Symbol | Annotation | Fold of modulation |
|---|---|---|---|---|
| 53 | BC011492 | 9130020G10Rik | RIKEN cDNA 9130020G10 gene | 21.8 |
| 54 | BC031731 | Ehd2 | Similar to EH-domain containing 2 | 4.3 |
| 55 | BC031824 | Fkbp2 | FK506 binding protein 2 (13 kDa) | 16.5 |
| 56 | BC003219 | Trim27 | Similar to ret finger protein | 9.1 |
| 57 | BC029209 | D11Lgp2e | DNA segment, Chr 11, Lothar Hennighausen 2, expressed | 20.0 |
| 58 | BC016505 | Ephb4 | | 18.5 |
| 59 | BC023802 | | Similar to hypothetical protein FLJ11000 | 19.9 |
| 60 | BC012960 | Rnf12 | ring finger protein 12 | 15.3 |
| 61 | BC010702 | Mad1l1 | mitotic arrest deficient 1-like 1 | 9.7 |
| 62 | BC025098 | Prrg2 | Similar to proline-rich Gla (G-carboxyglutamic acid) polypeptide 2 | 14.5 |
| 63 | BC015523 | GSTA4 | glutathione S-transferase A4 | 11.7 |
| 64 | BC023498 | 1600025H15Rik | RIKEN cDNA 1600025H15 gene | 8.6 |
| 65 | BC033358 | MGC36472 | hypothetical protein MGC36472 | 8.7 |
| 66 | BC031888 | Mgmt | 0-6-methylguanine-DNA methyltransferase | 4.6 |
| 67 | BC019735 | Usp20 | | 8.2 |
| 68 | BC031112 | Fxyd5 | Similar to FXYD domain-containing ion transport regulator 5 | 7.7 |
| 69 | BC007134 | Uchrp | ubiquintin c-terminal hydrolase related polypeptide | 7.4 |
| 70 | BC019217 | 5031409J19Rik | | 7.5 |
| 71 | BC028050 | KIAA0616 | Similar to KIAA0616 protein | 9.5 |
| 72 | BC027381 | P2ry12 | purinergic receptor P2Y, G-protein coupled 12 | 7.2 |
| 73 | BC023690 | Htr2b | Similar to 5-hydroxytryptamine (serotonin) receptor 2B | 10.6 |
| 74 | BC029065 | Creld1 | expressed sequence AI843811 | 7.2 |
| 75 | BC018559 | Litaf | LPS-induced TNF-alpha factor | 7.6 |
| 76 | BC013643 | ORF1-FL49 | putative nuclear protein ORF1-FL49 | 8.9 |
| 77 | BC004845 | Ophn1 | Similar to oligophrenin 1 | 7.1 |
| 78 | BC005713 | Hdgf | | 7.0 |
| 79 | BC024110 | MGC36317 | Similar to solute carrier family 35 (UDP-N-acetylglucosamine (UDP-GlcNAc) transporter), member 3 | 5.3 |
| 80 | BC018258 | MGC36472 | | 6.8 |
| 81 | BC024111 | MGC7221 | CGI-78 protein | 5.1 |
| 82 | BC019384 | D17Wsu94e | | 5.9 |
| 83 | BC010505 | SCAMP3 | Similar to secretory carrier membrane protein 3 | 3.8 |
| 84 | BC014772 | Uba52 | ubiquitin A-52 residue ribosomal protein fusion product 1 | 5.9 |
| 85 | BC010298 | Gna-rs1 | | 7.5 |
| 86 | BC003317 | 2610311I19Rik | Similar to RIKEN cDNA 2310016N21 gene | 6.3 |
| 87 | BC021654 | Hdgf | | 7.2 |
| 88 | BC014743 | MGC25673 | | 6.3 |
| 89 | BC027854 | VRK2 | vaccinia related kinase 2 | 3.4 |
| 90 | BC021626 | Nsbp1 | nucleosome binding protein 1 | 7.0 |
| 91 | BC034558 | AU018638 | expressed sequence AU018638 | 5.5 |
| 92 | BC022605 | Aibzip-pending | RIKEN cDNA 5330432F22 gene | 4.7 |
| 93 | BC010789 | onzin | Similar to hypothetical protein | 5.7 |
| 94 | BC031383 | 6720407G21Rik | Similar to RIKEN cDNA 6720407G21 gene | 4.7 |
| 950 | BC011474 | Lck | Similar to lymphocyte-specific protein tyrosine kinase | 5.7 |
| 96 | BC029096 | Grtp1 | GH regulated TBC protein 1 | 3.3 |
| 97 | BC019570 | MGC28611 | Similar to G protein-coupled receptor 43 | 5.6 |
| 98 | BC003866 | Vapa | vesicle-associated membrane protein, associated protein A (33 kDa) | 5.2 |
| 99 | BC034595 | MGC36472 | | 5.1 |
| 100 | BC029859 | AB041616 | hypothetical protein, MNCb-3350 | 6.6 |
| 101 | BC012940 | C9orf9 | Similar to chromosome 9 open reading frame 9 | 5.3 |
| 102 | BC029661 | MGC36472 | | 4.8 |

TABLE 2-continued

Additional AP-1-modulators

| | MGC11k.GenBank | Symbol | Annotation | Fold of modulation |
|---|---|---|---|---|
| 103 | BC002021 | Scamp3 | Similar to secretory carrier membrane protein 3 | 5.4 |
| 104 | BC012205 | PLAC8 | Similar to hypothetical protein | 4.5 |
| 105 | BC029111 | | Similar to NICE-5 protein | 5.4 |
| 106 | BC018480 | MGC36472 | | 3.8 |
| 107 | BC017554 | ACTA2 | actin, alpha 2, smooth muscle, aorta | 3.9 |
| 108 | BC031367 | MGC36472 | | 6.7 |
| 109 | BC025571 | 2310005P05Rik | | 4.0 |
| 110 | BC014842 | NUP62 | | 2.7 |
| 111 | BC026784 | 1700023O11Rik | RIKEN cDNA 1700023O11 gene | 5.1 |
| 112 | BC033452 | Slc30a5-pending | Similar to zinc transporter ZTL1 | 4.0 |
| 113 | BC021517 | Gli5 | GLI-Kruppel family member GLI5 | 6.5 |
| 114 | BC004829 | Syngr2 | synaptogyrin 2 | 4.9 |
| 115 | BC026977 | Napg | | 4.3 |
| 116 | BC026946 | 2510004L20Rik | RIKEN cDNA 2510004L20 gene | 4.4 |
| 117 | BC023748 | MGC31101 | | 6.2 |
| 118 | BC004849 | Stx5a | syntaxin 5a | 4.6 |
| 119 | BC012303 | DD96 | Similar to epithelial protein up-regulated in carcinoma, membrane associated protein 17 | 4.4 |
| 120 | BC003230 | 9430096L06Rik | RIKEN cDNA 9430096L06 gene | 4.6 |
| 121 | BC002300 | 4921519L13Rik | | 4.2 |
| 122 | BC002062 | Rpl29 | ribosomal protein L29 | 4.1 |
| 123 | BC013273 | Ptprcap | Similar to protein tyrosine phosphatase, receptor type, C-associated protein | 5.1 |
| 124 | BC018528 | MGC9850 | hypothetical gene supported by BC018528; BC015319 | 4.6 |
| 125 | BC012469 | | Similar to RIKEN cDNA A430107J06 gene | 4.2 |
| 126 | BC008158 | 2010008K16Rik | RIKEN cDNA 2010008K16 gene | 4.4 |
| 127 | BC012837 | BBX | | 3.8 |
| 128 | BC010336 | H2afx | H2A histone family, member X | 5.1 |
| 129 | BC021883 | Stx5a | | 3.2 |
| 130 | BC025932 | Creld1 | expressed sequence AI843811 | 3.5 |
| 131 | BC021435 | 2610319K07Rik | RIKEN cDNA 2610319K07 gene | 4.7 |
| 132 | BC031195 | | Similar to BTB domain protein BDPL | 4.0 |
| 133 | BC039279 | | Similar to neuronal guanine nucleotide exchange factor | 4.0 |
| 134 | BC019449 | 2810047M21Rik | | 4.2 |
| 135 | BC023924 | 1110057L18Rik | Similar to phytoceramidase, alkaline | 2.4 |
| 136 | BC016609 | CMAS | Similar to CMP-N-acetylneuraminic acid synthase | 4.2 |
| 137 | BC012959 | Stau1 | staufen (RNA-binding protein) homolog 1 (Drosophila) | 4.9 |
| 138 | BC002098 | LOC226591 | similar to CG9578 gene product | 3.9 |
| 139 | BC030295 | MGC40131 | similar to hypothetical protein, MGC: 8159; hypothetical protein MGC8159 | 2.5 |
| 140 | NM_006293 | TYRO3 | TYRO3 protein tyrosine kinase | |

Once test agents that modulate the AP-1-modulatory polypeptides are identified, they are typically further tested for ability to modulate AP-1 transcription factor activities. The test agent can be further tested for its ability to modulate expression or cellular level of AP-1 or its subunits. Alternatively, the test agent can be further tested for its activity on modulating transcription regulating function of AP-1, e.g., binding to an AP-1 recognition sequence or promoting expression of a gene under the control of an AP-1 binding sequence (i.e., AP-1 responsive gene).

As noted above, the AP-1-modulatory polypeptides identified by the present inventors can modulate cellular level of AP-1 or transcription-regulating functions of AP-1. If a test agent identified in the first screening step modulates cellular level (e.g., by altering transcription activity) of the AP-1-modulatory polypeptide, it would indirectly modulate the AP-1 transcription factor. For example, if the AP-1-modulatory polypeptide (e.g., a kinase) modulates AP-1 activities by specifically phosphorylating AP-1 or its subunits, a test agent which alters cellular level of the AP-1-modulatory kinase would indirectly also modulate AP-1 activities. Similarly, if the AP-1-modulatory polypeptide modulates cellular level of an AP-1 subunit, a test agent that modulates cellular level of the AP-1-modulatory polypeptide would indirectly alter cellular level of the AP-1 subunit.

On the other hand, if a test agent modulates an activity other than cellular level of the AP-1-modulatory polypeptide, then the further testing step is needed to confirm that their modulatory effect on the AP-1-modulatory polypeptide would indeed lead to modulation of AP-1 activities (e.g., cellular level of AP-1 or transcription regulating function of AP-1). For example, a test agent, which modulates phosphorylation activity of an AP-1-modulatory polypeptide, needs to be further tested in order to confirm that modulation of phosphorylation activity of the AP-1-modulatory polypeptide can result in modulation of AP-1 transcription regulating function or AP-1 cellular level.

In both the first assaying step and the second testing step, either an intact AP-1-modulatory polypeptide and AP-1 transcription factor or subunits or their fragments, analogs, or functional derivatives can be used. The fragments that can be employed in these assays usually retain one or more of the biological activities of the AP-1-modulatory polypeptide (e.g., kinase activity if the AP-1-modulatory employed in the first assaying step is a kinase) and AP-1 (e.g., binding to an AP-1 recognition sequence). Fusion proteins containing such fragments or analogs can also be used for the screening of test agents. Functional derivatives of AP-1-modulatory polypeptide and AP-1 transcription factor usually have amino acid deletions and/or insertions and/or substitutions while maintaining one or more of the bioactivities and therefore can also be used in practicing the screening methods of the present invention.

A functional derivative can be prepared from a naturally occurring or recombinantly expressed AP-1-modulatory polypeptide or AP-1 subunit by proteolytic cleavage followed by conventional purification procedures known to those skilled in the art. Alternatively, the functional derivative can be produced by recombinant DNA technology by expressing only fragments of an AP-1-modulatory polypeptide or an AP-1 subunit that retain one or more of their bioactivities.

A variety of well-known techniques can be used to identify test agents that modulate an AP-1-modulatory polypeptide or an AP-1 transcription factor. Preferably, the test agents are screened with a cell based assay system. For example, in a typical cell based assay for screening AP-1 modulators (i.e., the second screening step), a construct comprising an AP-1 transcription regulatory element operably linked to a reporter gene is introduced into a host cell system. The activity of polypeptide encoded by the reporter gene (i.e., reporter polypeptide), e.g., an enzymatic activity, in the presence of a test agent can be determined and compared to the activity of the reporter polypeptide in the absence of the test agent. An increase or decrease in the activity identifies a modulator of AP-1. The reporter gene can encode any detectable polypeptide (response or reporter polypeptide) known in the art, e.g., detectable by fluorescence or phosphorescence or by virtue of its possessing an enzymatic activity. The detectable response polypeptide can be, e.g., luciferase, alpha-glucuronidase, alpha-galactosidase, chloramphenicol acetyl transferase, green fluorescent protein, enhanced green fluorescent protein, and the human secreted alkaline phosphatase.

In the cell-based assays, the test agent (e.g., a peptide or a polypeptide) can also be expressed from a different vector that is also present in the host cell. In some methods, a library of test agents are encoded by a library of such vectors (e.g., a cDNA library; see the Example below). Such libraries can be generated using methods well known in the art (see, e.g., Sambrook et al. and Ausubel et al., supra) or obtained from a variety of commercial sources.

In addition to cell based assays described above, modulators of AP-1 can also be screened with non-cell based methods. These methods include, e.g., mobility shift DNA-binding assays, methylation and uracil interference assays, DNase and hydroxy radical footprinting analysis, fluorescence polarization, and UV crosslinking or chemical cross-linkers. For a general overview, see, e.g., Ausubel et al., supra (chapter 12, DNA-Protein Interactions). One technique for isolating co-associating proteins, including nucleic acid and DNA/RNA binding proteins, includes use of UV crosslinking or chemical cross-linkers, including e.g., cleavable cross-linkers dithiobis (succinimidylpropionate) and 3,3'-dithiobis (sulfosuccinimidyl-propionate); see, e.g., McLaughlin (1996) Am. J. Hum. Genet. 59:561-569; Tang (1996) Biochemistry 35:8216-8225; Lingner (1996) Proc. Natl. Acad. Sci. USA 93:10712; Chodosh (1986) Mol. Cell. Biol 6:4723-4733.

B. Test Agents

Test agents that can be screened with methods of the present invention include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test agents are synthetic molecules, and others natural molecules.

Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be naturally occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the test agents are polypeptides or proteins.

The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small molecules (e.g., molecules with a molecular weight of not more than about 1,000). Preferably, high throughput assays are adapted and used to screen for such small molecules. In some methods, combinatorial libraries of small molecule test agents as described above can be readily employed to screen for small molecule modulators of AP-1. A number of assays are available for such screening, e.g., as described in Schultz (1998) Bioorg Med Chem Lett 8:2409-2414; Weller (1997) Mol Divers. 3:61-70; Fernandes (1998) Curr Opin Chem Biol 2:597-603; and Sittampalam (1997) Curr Opin Chem Biol 1:384-91.

Libraries of test agents to be screened with the claimed methods can also be generated based on structural studies of the AP-1-modulatory polypeptides discussed above, an AP-1 transcription factor or its subunit. Such structural studies allow the identification of test agents that are more likely to bind to the AP-1-modulatory polypeptides. The three-dimensional structures of the AP-1-modulatory polypeptides or an AP-1 subunit can be studied in a number of ways, e.g., crystal structure and molecular modeling. Methods of studying protein structures using x-ray crystallography are well known in the literature. See Physical Bio-chemistry, Van Holde, K. E. (Prentice-Hall, New Jersey 1971), pp. 221-239, and Physical Chemistry with Applications to the Life Sciences, D. Eisenberg & D. C. Crothers (Benjamin Cummings, Menlo Park 1979). Computer modeling of AP-1-modulatory polypeptides' structures provides another means for designing test agents for screening AP-1 modulators. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR). See, e.g., Physical Chemistry, 4th Ed. Moore, W. J. (Prentice-Hall, New Jersey 1972), and NMR of Proteins and Nucleic Acids, K. Wuthrich (Wiley-Interscience, New York 1986).

Modulators of the present invention also include antibodies that specifically bind to an AP-1-modulatory polypeptide in Table 1 or 2. Such antibodies can be monoclonal or polyclonal. Such antibodies can be generated using methods well known in the art. For example, the production of non-human monoclonal antibodies, e.g., murine or rat, can be accomplished by, for example, immunizing the animal with an AP-1-modulatory polypeptide or its fragment (See Harlow & Lane, Antibodies, A Laboratory Manual, Cold Spring Harbor Laboratory Press, Cold Spring Harbor N.Y.). Such an immunogen can be obtained from a natural source, by peptides synthesis or by recombinant expression.

Humanized forms of mouse antibodies can be generated by linking the CDR regions of non-human antibodies to human constant regions by recombinant DNA techniques. See Queen et al., Proc. Natl. Acad. Sci. USA 86, 10029-10033 (1989) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to an AP-1-modulatory polypeptide.

Human antibodies against an AP-1-modulatory polypeptide can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using an AP-1-modulatory polypeptide or its fragment.

C. Screening Test Agents that Modulate AP-1-modulatory Polypeptides

A number of assay systems can be employed to screen test agents for modulators of an AP-1-modulatory polypeptide. As noted above, the screening can utilize an in vitro assay system or a cell-based assay system. In this screening step, test agents can be screened for binding to the AP-1-modulatory polypeptide, altering cellular level of the AP-1-modulatory polypeptide, or modulating other biological activities of the AP-1-modulatory polypeptide.

1. Binding of Test Agents to an AP-1-modulatory Polypeptide

In some methods, binding of a test agent to an AP-1-modulatory polypeptide is determined in the first screening step. Binding of test agents to an AP-1-modulatory polypeptide can be assayed by a number of methods including e.g., labeled in vitro protein-protein binding assays, electrophoretic mobility shift assays, immunoassays for protein binding, functional assays (phosphorylation assays, etc.), and the like. See, e.g., U.S. Pat. Nos. 4,366,241; 4,376,110; 4,517,288; and 4,837,168; and also Bevan et al., Trends in Biotechnology 13:115-122, 1995; Ecker et al., Bio/Technology 13:351-360, 1995; and Hodgson, Bio/Technology 10:973-980, 1992. The test agent can be identified by detecting a direct binding to the AP-1 modulatory polypeptide, e.g., co-immunoprecipitation with the AP-1-modulatory polypeptide by an antibody directed to the AP-1-modulatory polypeptide. The test agent can also be identified by detecting a signal that indicates that the agent binds to the AP-1-modulatory polypeptide, e.g., fluorescence quenching.

Competition assays provide a suitable format for identifying test agents that specifically bind to an AP-1-modulatory polypeptide. In such formats, test agents are screened in competition with a compound already known to bind to the AP-1-modulatory polypeptide. The known binding compound can be a synthetic compound. It can also be an antibody, which specifically recognizes the AP-1-modulatory polypeptide, e.g., a monoclonal antibody directed against the AP-1-modulatory polypeptide. If the test agent inhibits binding of the compound known to bind the AP-1-modulatory polypeptide, then the test agent also binds the AP-1-modulatory polypeptide.

Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using $^{125}$I label (see Morel et al., Mol. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified polypeptide bound to a solid surface or cells bearing either of these, an unlabelled test agent and a labeled reference compound. Competitive inhibition is measured by determining the amount of label bound to the solid surface or cells in the presence of the test agent. Usually the test agent is present in excess. Modulating agents identified by competition assay include agents binding to the same epitope as the reference compound and agents binding to an adjacent epitope sufficiently proximal to the epitope bound by the reference compound for steric hindrance to occur. Usually, when a competing agent is present in excess, it will inhibit specific binding of a reference compound to a common target polypeptide by at least 50 or 75%.

The screening assays can be either in insoluble or soluble formats. One example of the insoluble assays is to immobilize an AP-1-modulatory polypeptide or its fragments onto a solid phase matrix. The solid phase matrix is then put in contact with test agents, for an interval sufficient to allow the test agents to bind. Following washing away any unbound material from the solid phase matrix, the presence of the agent bound to the solid phase allows identification of the agent. The methods can further include the step of eluting the bound agent from the solid phase matrix, thereby isolating the agent. Alternatively, other than immobilizing the AP-1-modulatory polypeptide, the test agents are bound to the solid matrix and the AP-1-modulatory polypeptide molecule is then added.

Soluble assays include some of the combinatory libraries screening methods described above. Under the soluble assay formats, neither the test agents nor the AP-1-modulatory polypeptide are bound to a solid support. Binding of an AP-1-modulatory polypeptide or fragment thereof to a test agent can be determined by, e.g., changes in fluorescence of either the AP-1-modulatory polypeptide or the test agents, or both. Fluorescence may be intrinsic or conferred by labeling either component with a fluorophor.

In some binding assays, either the AP-1-modulatory polypeptide, the test agent, or a third molecule (e.g., an antibody against the AP-1-modulatory polypeptide) can be provided as labeled entities, i.e., covalently attached or linked to a detectable label or group, or cross-linkable group, to facilitate identification, detection and quantification of the polypeptide in a given situation. These detectable groups can comprise a detectable polypeptide group, e.g., an assayable enzyme or antibody epitope. Alternatively, the detectable group can be selected from a variety of other detectable groups or labels, such as radiolabels (e.g., $^{125}$I, $^{32}$P, $^{35}$S) or a chemiluminescent or fluorescent group. Similarly, the detectable group can be a substrate, cofactor, inhibitor or affinity ligand.

2. Agents Modulating Other Activities of AP-1-modulatory Polypeptides

Binding of a test agent to an AP-1-modulatory polypeptide provides an indication that the agent can be a modulator of the AP-1-modulatory polypeptide. It also suggests that the agent may modulate AP-1 transcription factor activity (e.g., by binding to and modulate the AP-1-modulatory polypeptide which in turn acts on AP-1). Thus, a test agent that binds to an AP-1-modulatory polypeptide can be further tested for ability to modulate AP-1 transcription factor activities (i.e., in the second testing step outlined above).

Alternatively, a test agent that binds to an AP-1-modulatory polypeptide can be further examined to determine its activity on the AP-1-modulatory polypeptide. The existence, nature, and extent of such activity can be tested by an activity assay. Such an activity assay can confirm that the test agent binding to the AP-1-modulatory polypeptide indeed has a modulatory activity on the AP-1-modulatory polypeptide. More often, such activity assays can be used independently to identify test agents that modulate activities of an AP-1-modulatory polypeptide (i.e., without first assaying their ability to bind to the AP-1-modulatory polypeptide). In general, such methods involve adding a test agent to a sample containing an AP-1-modulatory polypeptide in the presence or absence of other molecules or reagents which are necessary to test a biological activity of the AP-1-modulatory polypeptide (e.g., kinase activity if the AP-1-modulatory polypeptide is a kinase), and determining an alteration in the biological activity of the AP-1-modulatory polypeptide. In addition to assays for screening agents that modulate an enzymatic or other biological activities of an AP-1-modulatory polypeptide, the activity assays also encompass in vitro screening and in vivo screening for alterations in expression or cellular level of the AP-1-modulatory polypeptide.

In an exemplary embodiment, the AP-1-modulatory polypeptide is a kinase, and the test agent is examined for ability to modulate the kinase activity of the AP-1-modulatory polypeptide. Methods for monitoring kinase activity and AP-1 phosphorylation are described, e.g., in Chedid et al., J. Immunol. 147: 867-73, 1991; Kontny et al., Eur J. Pharmacol. 227: 333-8, 1992; Wang et al., Oncogene 13: 2639-47, 1996; Murakami et al., Oncogene 14: 2435-44, 1997; Pyrzynska et al., J. Neurochem.74: 42-51, 2000; and Berry et al., Biochem Pharmacol. 62: 581-91, 2001. Any of these methods can be employed to assay modulatory effect of a test agent on an AP-1-modulatory polypeptide (e.g., one encoded by Accession No. NM_033015.1, XM_034315.1, or XM_166235.1).

D. Screening Agents that Modulate AP-1 Transcription Factor Activities

Once a modulating agent has been identified to bind to an AP-1-modulatory polypeptide and/or to modulate a biological activity (including cellular level) of the AP-1-modulatory polypeptide, it can be further tested for ability to modulate activities of AP-1 transcription factor. Modulation of activities of the AP-1 transcription factor by the modulating agent is typically tested in the presence of the AP-1-modulatory polypeptide. When a cell-based screening system is employed, the AP-1-modulatory polypeptide can be expressed from an expression vector that has been introduced into a host cell. AP-1 or an AP-1 subunit can be expressed from a second expression vector. Alternatively, AP-1 or an AP-1 subunit can be supplied endogenously by the host cell in the screening system.

In some embodiments, this testing step does not employ an AP-1 transcription factor or an AP-1 subunit. Instead, a transcription regulatory element (e.g., an AP-1 binding element or other transcription regulatory element) from genes encoding AP-1 subunits (e.g., fos or jun) is tested for directing expression of a reporter gene in the presence of the test agent identified in the first screening step.

1. Activities of AP-1 Transcription Factor

Unless otherwise specified, modulation of AP-1 transcription factor includes modulation of cellular level of AP-1 transcription factor or its subunits, as well as other biological or cellular activities of AP-1 transcription factor or its subunits. The term "AP-1 bioactivity" or "biological activity of AP-1" refers to the biochemical and physiological roles played by an AP-1 transcription factor in regulating cellular processes. The AP-1 transcription factor is involved in a very broad range of biological pathways and cellular activities (see, e.g., Kaminska et al., Acta Neurobiol Exp 60: 395-402, 2000). For example, AP-1 transcription factor plays a role in cell proliferation and neuronal activation. It is also involved in apoptosis of cells in response to stress, DNA damaging agents or lack of survival signals.

All these activities can be tested in the presence of a test agent that has been identified to bind to and/or modulate an AP-1-modulatory polypeptide. In addition, as noted above, activities of an AP-1 transcription factor to be monitored in this screening step include activities relating to cellular levels of AP-1 or its subunits (e.g., transcription expression), enzymatic or non-enzymatic modification of AP-1 protein complex or subunits, biochemical activities of expressed AP-1 proteins (binding to an AP-1 binding site or responsive element).

2. Screening for Modulators of AP-1 Transcription Factor

Modulation of cellular level or other activities of an AP-1 transcription factor or its subunits can be determined in a non-cell based assay system or cell-based assays, similar to the first screening step for identifying modulators of AP-1-modulatory polypeptides. Using eukaryotic in vitro transcription systems, effects of test agents on AP-1 level or activities can be tested by directly measuring in the presence of the test agents expression of AP-1 subunits (e.g., Jun or Fos), cellular level of AP-1 protein complex, or transcription regulating activity of AP-1 transcription factor. Because the test agent is likely to exert its modulatory effect on AP-1 by modulating an AP-1-modulatory polypeptide, the AP-1-modulatory polypeptide is typically also present in the assay system.

With cell-based assays, vectors expressing a reporter gene or other linked polynucleotides (e.g., one encoding an AP-1 subunit or its fragment) under the control of an AP-1 transcription regulatory element (e.g., a promoter or an enhancer sequence) are introduced into appropriate host cells. Modulation of AP-1 activities are typically examined by measuring expression of the reporter genes or other linked polynucleotides. An altered activity of the reporter gene (e.g., its cellular level) in the presence of a test agent would indicate that the test agent is a modulator of the AP-1 activity. If endogenous AP-1 transcription factor is present in the host cell, modulation of the reporter gene expression by a test agent can be direct, e.g., by binding to the AP-1 transcription regulatory element. The modulation can also be indirect, e.g., through interacting with another molecule (e.g., an AP-1 modulatory polypeptide or AP-1 itself), which in turn binds to the AP-1 transcription regulatory element (e.g., an AP-1 recognition sequence).

Various assays for analyzing activities of AP-1 transcription factor have been described in the art and can be readily employed to screen for test agents that modulate AP-1 activities. For example, expression of AP-1 subunits or cellular levels of AP-1 complex can be measured using routinely practiced methods (e.g., Sambrook et al., supra; and Ausubel et al., supra), as well as numerous methods described in the literatures (e.g., Kvanta et al., Cell Signal 4: 275-86, 1992). In vitro or in vivo assays for testing a test agent's ability to modulate AP-1 activities can also be performed as described in, e.g., Shaulian et al., Oncogene 20:2390-400, 2001; Lee et al., Anticancer Res 18:119-24, 1998; Rezzonico et al., Oncogene 11:1069-78, 1995; Fanjul et al., Nature 372:107-11, 1994; and Angel et al., Biochim Biophys Acta, 1072: 29-57, 1991.

Members of the AP-1 family subunits and their transcription regulatory elements have been well known and characterized in the art (see, e.g., The FOS and JUN Families of Proteins, Angel and Herrlich, eds., CRC Press, Boca Raton, Fla., 1994; Nicolaides et al., J. Biol. Chem. 267: 19665-72, 1992; and SteinmÃller et al., Biochem J, 360: 599-607, 2001). Other than the auto-regulating AP-1 recognition sequences present in genes encoding AP-1 subunits (e.g., c-jun and c-fos), other transcription regulatory elements of AP-1 subunits have also been described in the art, e.g., Marx et al., Science 237:854-856, 1987; Lee et al., Cell 49:741-752, 1987; Hirai et al., EMBO J, 8: 1433-9, 1989; Nishina et al., Proc Natl Acad Sci USA, 87(9): 3619-23, 1990; SchÃnthal et al., New Biol, 2(2): 143-50, 1990; SchÃnthal et al., New Biol, 3: 977-86, 1991; and Unlap et al., Nucleic Acids Res, 20: 897-902, 1992. All these transcription regulatory elements can be employed in the present invention to test an agent's ability to modulate AP-1 transcription regulating activities or AP-1 expression activities.

For example, similar to the first screening step, modulation of AP-1 promoter/enhancer activity can be examined in a cell-based system by transient or stable transfection of an expression vector into cultured cell lines. Assay vectors bearing AP-1 promoter or enhancer sequences (e.g., an AP-1 recognition sequence) operably linked to reporter genes can be transfected into any mammalian cell line (e.g., HEK 293 cell line as described in the Examples) for assays of promoter activity. General methods of cell culture, transfection, and reporter gene assay have been described in the art, e.g., Ausubel, supra; and Transfection Guide, Promega Corporation, Madison, Wis. (1998). Any readily transfectable mammalian cell line can be used to assay AP-1 promoter, e.g., HEK 293, MCF-7, and HepG2 are all suitable cell lines.

Constructs containing an AP-1 transcription regulatory element operably linked to a reporter gene can be prepared using only routinely practiced techniques and methods of molecular biology (see, e.g., Sambrook et al. and Ausubel et al., supra). Various transcription regulatory elements of AP-1 subunits can be employed in the present invention. For example, an enhancer element or the promoter sequence of the well characterized c-Jun or c-Fos as described above can be used to construct such expression vectors. Other than c-Jun or c-Fos, transcription regulatory elements of other AP-1 subunits (e.g., Jun D or Fra) can also be employed to construct the expression vectors. Alternatively, expression vectors containing a reporter gene under the control of a transcription regulatory element of an AP-1 subunit can also be obtained commercially (e.g., from Clontech, Palo Alto, Calif.; see the Example below).

When inserted into the appropriate host cell, the AP-1 promoter or enhancer sequence (e.g., an AP-1 recognition sequence) induces transcription of the reporter gene by host RNA polymerases. Reporter genes typically encode polypeptides with an easily assayed enzymatic activity that is naturally absent from the host cell. Typical reporter polypeptides for eukaryotic promoters include, chloramphenicol acetyltransferase (CAT), firefly or Renilla luciferase, beta-galactosidase, beta-glucuronidase, alkaline phosphatase, and green fluorescent protein (GFP).

Transcription driven by AP-1 promoter or enhancer sequences (e.g., an AP-1 recognition sequence) may also be detected by directly measuring the amount of RNA transcribed from the reporter gene. In these embodiments, the reporter gene may be any transcribable nucleic acid of known sequence that is not otherwise expressed by the host cell. RNA expressed from constructs containing an AP-1 promoter and/or enhancer may be analyzed by techniques known in the art, e.g., reverse transcription and amplification of mRNA, isolation of total RNA or poly $A^+$ RNA, northern blotting, dot blotting, in situ hybridization, RNase protection, primer extension, high density polynucleotide array technology and the like. These techniques are all well known and routinely practiced in the art.

In addition to reporter genes, vectors for assaying AP-1 promoter or enhancer activity can also comprise elements necessary for propagation or maintenance in the host cell, and elements such as polyadenylation sequences and transcriptional terminators to increase expression of reporter genes or prevent cryptic transcriptional initiation elsewhere in the vector. Exemplary assay vectors are the pGL3 series of vectors (Promega, Madison, Wis.; U.S. Pat. No. 5,670, 356), which include a polylinker sequence 5' of a luciferase gene. AP-1 promoter fragments may be inserted into the polylinker sequence and tested for luciferase activity in the appropriate host cell. Assay vectors may also comprise additional enhancer or promoter sequences, depending on whether the AP-1 transcription regulatory elements are sufficient to drive transcription of the reporter genes. For example, in addition to the AP-1 recognition sequence, the expression vectors can contain additional promoter sequence such as a minimal promoter (e.g., a promoter derived from Herpes simplex virus thymidine kinase) as discussed in Example 1.

If the AP-1 transcription regulatory sequence in the vector does not contain transcription initiation elements, an assay vector such as pGL3-Promoter may be used. This vector has transcription initiation elements from the SV40 promoter. In such vectors, transcription initiates from a heterologous site but the rate of transcription is increased by the presence of linked AP-1 promoter or enhancer elements.

3. Agents Modulating AP-1 Responsive Genes

Other than monitoring AP-1 transcription factor activity, a test agent, which modulates an AP-1-modulatory polypeptide, can be further screened for ability to modulate cellular proliferation through modulating AP-1 activity. In some methods, the test agent can be identified based on modulation of a cellular proliferation phenotype, e.g., inhibition of cell proliferation, cell or tumor growth arrest, or cell death. As discussed above, AP-1 activities in promoting cellular proliferation are well known, and methods for measuring such activities have also been described in the art.

In some methods, a test agent, which modulate an AP-1-modulatory polypeptide and/or modulate AP-1 transcription factor can be further examined for effects on expression of AP-1 responsive genes. Expression of a great number of genes are known to be regulated by the AP-1 transcription factor. These genes are involved in many important cell processes such as DNA synthesis and repair processes, RNA transcription, and cisplatin resistance. For example, AP-1 responsive genes include metallothionein, DNA polymerase 13, thymidylate synthase, dTMP synthase, topoisomerase I, topoisomerase II, and glutathione-S-transferase. Other genes regulated by AP-1 or containing AP-1 recognition site(s) includes hepatocyte growth factor receptor (c-met) gene (Seol et al., Oncogene 19:1132-7, 2000); human complement factor I gene (Minta et al., Mol Cell Biochem 201: 111-23, 1999); human SPRR1A keratinocyte terminal differentiation marker (Sark et al., J Biol Chem 273: 24683-92, 1998); human decorin gene (Mauviel et al., J Biol Chem 271: 24824-9, 1996); human heme oxygenase gene (Takeda et al., J Biol Chem 269: 22858-67, 1994); human spr1 gene (An et al., J Biol Chem 268: 10977-82, 1993); human stromelysin gene (Buttice et al., Nucleic Acids Res 19: 3723-31, 1991); tyrosine hydroxylase gene (Icard-Liepkalns et al., J Neurosci Res 32: 290-8, 1992); human osteocalcin gene (Schule et al., Cell 61: 497-504, 1990); human glutathione S-transferase-pi gene (Morrow et al., Gene 75: 3-11, 1989); vasoactive intestinal peptide gene (Hahm et al., J Biol Chem 274: 25588-93, 1999); proenkephalin gene (Monnier et al., DNA Cell Biol 17: 151-9, 1998); gonadotropin-releasing hormone (GnRH) gene (Zakaria et al., Mol Endocrinol 10: 1282-91, 1996); human NAD(P)H:quinone oxidoreductase (NQO1) gene (Wang et al., Biochim Biophys Acta 1307: 104-10, 1996); and human chromogranin A gene (Nolan et al., Mol Cell Endocrinol 124: 51-62, 1996). AP-1 modulators of the present invention can be used to identify agents that can modulate these AP-1 responsive genes and the cellular processes mediated by these genes.

IV. Modulation of AP-1 Activity In Vivo

The present invention provides compositions and methods for modulating activities of AP-1 transcription factor or its subunits (e.g., Jun and Fos) in a cell, and for modulating cellular proliferation. As a consequence of the connection between cellular proliferation and AP-1 transcription factor (e.g., the heterodimer of c-Fos and c-Jun), modulation of cellular levels or activities of AP-1 transcription factor can lead to modulation of cellular proliferation. Modulation by the AP-1 modulators of the present invention (polypeptides or other molecules) can act through a number of mechanisms. The modulation can either be a decrease or an increase in an AP-1 promoter (e.g., of c-fos or c-jun) activity. For example, expression of AP-1 subunits may be decreased or increased by binding of an AP-1 modulator to their promoter sequences. If desired, modulation of one subunit can be combined with modulation of another AP-1 subunit in order to achieve a requisite degree of effect upon AP-1-mediated transcription. In some methods, modulation of cellular proliferation by AP-1 modulators of the present invention is achieved through modulating other biological activities of AP-1, e.g., the transcription regulating activity.

To modulate AP-1 activity in vivo, a cell can be contacted with any a number of the AP-1 modulators identified in accordance with the present invention. In some methods, a modulator of AP-1 of the present invention is introduced directly to a subject (e.g., a human or a non-human animal). In some methods, a polynucleotide encoding a modulator of AP-1 of the present invention is introduced by retroviral or other means (as detailed below). For example, the polynucleotides shown in Tables 1 and 2 or their fragments can be used to modulate AP-1 activity in vivo.

Activities of AP-1 modulators of the present invention can be examined or further verified in vivo by employing transgenic animals. Accordingly, transgenic animals with integrated AP-1 promoter or enhancer sequences (e.g., an AP-1 recognition sequence) can be used to assay modulation of AP-1 transcription factor activities in vivo. Transgenic animals (e.g., transgenic mice) expressing AP-1 promoter/enhancer sequences or AP-1 recognition sequences can be generated according to methods well known in the art. For example, techniques routinely used to create and screen for transgenic animals have been described in, e.g., see Bijvoet (1998) Hum. Mol. Genet. 7:53-62; Moreadith (1997) J. Mol. Med. 75:208-216; Tojo (1995) Cytotechnology 19:161-165;

Mudgett (1995) Methods Mol. Biol. 48:167-184; Longo (1997) Transgenic Res. 6:321-328; U.S. Pat. No. 5,616,491 (Mak, et al.); U.S. Pat. Nos. 5,464,764; 5,631,153; 5,487,992; 5,627,059; 5,272,071; and, WO 91/09955, WO 93/09222, WO 96/29411, WO 95/31560, and WO 91/12650.

In some embodiments, an AP-1 promoter or enhancer sequence (e.g., an AP-1 recognition sequence) or an AP-1 binding site, linked either to a reporter gene or to native AP-1 subunit coding sequence, is injected into the embryo of a developing animal (typically a mouse) to generate a transgenic animal. Once integration of the transgene has been verified, tissues of the animal (e.g., lymphoid tissues) are then assayed for expression of the transgene. For example, where the AP-1 promoter/enhancer sequence or an AP-1 binding site is linked to a reporter gene, tissues of the transgenic animal may be assayed either for reporter gene RNA or for the enzymatic activity of the reporter protein.

In the transgenic animals, AP-1 promoter or enhancer sequences or AP-1 recognition sequences will generally display appropriate regulation regardless of the site of transgene integration. However, constructs comprising the regulatory sequences can also be flanked by insulator elements to ensure complete independence from position effects (see Bell et al., Science 291:447-50, 2001).

V. Therapeutic Applications

AP-1 transcription factor plays an important role in cellular proliferation. Many clinical conditions or disease states are linked to abnormal cell proliferation. Such disease states and disorders include those involving the hyperproliferation of cells such as, e.g., a tumor (neoplasm) or malignant tumor. Tumors are abnormal growths resulting from the hyperproliferation of cells. Cells that proliferate to excess but stay put form benign tumors, which can typically be removed by local surgery. In contrast, malignant tumors or cancers comprise cells that are capable of undergoing metastasis, i.e., a process by which hyperproliferative cells spread to, and secure themselves within, other parts of the body via the circulatory or lymphatic system (see, generally, Chapter 16 In: Molecular Biology of the Cell, Alberts et al., eds., pp. 891-950, Garland Publishing, Inc., New York, 1983).

For example, it is known that several genes encoding enzymes required for metastasis are positively regulated by AP-1 (see, e.g., U.S. Pat. No. 6,312,900). Accordingly, inhibition of expression of AP-1 subunits (e.g., c-fos and/or c-jun) or AP-1 transcription factor activities serves as a means to modulate the metastasis of malignant tumors. Modulation of AP-1 cellular levels or activities can lead to inhibition of AP-1-mediated hyperproliferation of cells and provide prophylactic, palliative and therapeutic effects in subjects with such diseases and conditions.

Accordingly, the invention provides therapeutic compositions and methods for preventing or treating diseases and conditions due to abnormal cellular level or other activities of AP-1 transcription factor. The compositions and methods are useful for treating or modulating various hyperproliferative disorders or diseases, such as various cancers. Modulation of AP-1 activity or cellular levels is also useful for preventing or modulating the development of such diseases or disorders in an animal suspected of being, or known to be, prone to such diseases or disorders. The pharmaceutical compositions can comprise a polypeptide modulator of AP-1 identified in accordance with the present invention (e.g., as shown in Table 1 or 2), an antibody against such modulators, or other modulators disclosed herein which directly or indirectly modulate AP-1 transcription factor activities.

A. Examples of Disease and Conditions Amenable to Treatment

A great number of diseases and conditions are amenable to treatment with methods and compositions of the present invention. For example, AP-1 is a transcriptional activator of the gene encoding collagenase, and collagenase is one of the enzymes known to break down collagen, a component of bone. Thus, the control of AP-1 mediated transcription can be utilized to treat arthritis. Likewise, the control of AP-1 mediated transcription can also be utilized to treat tumors wherein AP-1 or an AP-1 subunit (e.g., Jun or Fos) plays a role.

Examples of tumors that can be treated with methods and compositions of the present invention include but are not limited to skin, breast, brain, cervical carcinomas, testicular carcinomas. They encompass both solid tumors or metastatic tumors. Cancers that can be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

Disease states other than cancer which can be treated by the methods and compositions also include restenosis, autoimmune disease, arthritis, graft rejection, inflammatory bowel disease, proliferation induced after medical procedures such as surgery, angioplasty, and the like. Other diseases and conditions are also know in the art which has implicated abnormal AP-1 activities. In some methods, cells not in a hyper or hypo proliferation state (abnormal state) are the subject of treatment. For example, during wound healing, the cells may be proliferating "normally", but proliferation enhancement may be desired. Similarly, in the agriculture arena, cells may be in a "normal" state, but proliferation modulation may be desired to enhance a crop by directly enhancing growth of a crop, or by inhibiting the growth of a plant or organism which adversely affects the crop. Thus, therapeutic applications of the present invention include treatment of individuals or agricultural crops with any one of these disorders or states.

B. Administration of Modulators of AP-1 Transcription Factor

1. Pharmaceutical Compositions

The AP-1 modulators of the present invention can be directly administered under sterile conditions to the subject to be treated. The modulators can be administered alone or as the active ingredient of a pharmaceutical composition. Therapeutic composition of the present invention can be combined with or used in association with other therapeutic agents. For example, a subject may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahay, N.J., 1987). When used with the compounds of the invention, such chemotherapeutic agents may be used individually, sequentially, or in combination with one or more other such chemotherapeutic agents.

Pharmaceutical compositions of the present invention typically comprise at least one active ingredient together with one or more acceptable carriers thereof. Pharmaceutically carriers enhance or stabilize the composition, or to facilitate preparation of the composition. Pharmaceutically acceptable carriers are determined in part by the particular composition being administered (e.g., nucleic acid, protein, modulatory compounds or transduced cell), as well as by the particular method used to administer the composition. They should also be both pharmaceutically and physiologically acceptable in the sense of being compatible with the other ingredients and not injurious to the subject. This carrier may take a wide variety of forms depending on the form of preparation desired for administration, e.g., oral, sublingual, rectal, nasal, or parenteral. For example, the AP-1 modulator can be complexed with carrier proteins such as ovalbumin or serum albumin prior to their administration in order to enhance stability or pharmacological properties.

There are a wide variety of suitable formulations of pharmaceutical compositions of the present invention (see, e.g., *Remington: The Science and Practice of Pharmacy*, Mack Publishing Co., 20$^{th}$ ed., 2000). Without limitation, they include syrup, water, isotonic saline solution, 5% dextrose in water or buffered sodium or ammonium acetate solution, oils, glycerin, alcohols, flavoring agents, preservatives, coloring agents-starches, sugars, diluents, granulating agents, lubricants, and binders, among others. The carrier may also include a sustained release material such as glyceryl monostearate or glyceryl distearate, alone or with a wax.

The pharmaceutical compositions can be prepared in various forms, such as granules, tablets, pills, suppositories, capsules, suspensions, salves, lotions and the like. The concentration of therapeutically active compound in the formulation may vary from about 0.1-100% by weight. Therapeutic formulations are prepared by any methods well known in the art of pharmacy. See, e.g., Gilman et al., eds., Goodman and Gilman's: The Pharmacological Bases of Therapeutics, 8th ed., Pergamon Press, 1990; Remington: The Science and Practice of Pharmacy, Mack Publishing Co., 20$^{th}$ ed., 2000; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

2. Modes of Administration

The therapeutic formulations can be delivered by any effective means which could be used for treatment. Depending on the specific AP-1 modulators to be administered, the suitable means include oral, rectal, vaginal, nasal, pulmonary administration, or parenteral (including subcutaneous, intramuscular, intravenous and intradermal) infusion into the bloodstream.

For parenteral administration, AP-1 modulators (including polynucleotides encoding AP-1 modulators) of the present invention may be formulated in a variety of ways. Aqueous solutions of the modulators may be encapsulated in polymeric beads, liposomes, nanoparticles or other injectable depot formulations known to those of skill in the art. The nucleic acids may also be encapsulated in a viral coat.

Additionally, the compounds of the present invention may also be administered encapsulated in liposomes. The compositions, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The compositions may be supplemented by active pharmaceutical ingredients, where desired. Optional antibacterial, antiseptic, and antioxidant agents may also be present in the compositions where they will perform their ordinary functions.

3. Dosages

The therapeutic formulations can conveniently be presented in unit dosage form and administered in a suitable therapeutic dose. A suitable therapeutic dose can be determined by any of the well known methods such as clinical studies on mammalian species to determine maximum tolerable dose and on normal human subjects to determine safe dosage. Except under certain circumstances when higher dosages may be required, the preferred dosage of an AP-1 modulator usually lies within the range of from about 0.001 to about 1000 mg, more usually from about 0.01 to about 500 mg per day.

The preferred dosage and mode of administration of an AP-1 modulator can vary for different subjects, depending upon factors that can be individually reviewed by the treating physician, such as the condition or conditions to be treated, the choice of composition to be administered, including the particular AP-1 modulator, the age, weight, and response of the individual subject, the severity of the subject's symptoms, and the chosen route of administration. As a general rule, the quantity of an AP-1 modulator administered is the smallest dosage which effectively and reliably prevents or minimizes the conditions of the subjects. Therefore, the above dosage ranges are intended to provide general guidance and support for the teachings herein, but are not intended to limit the scope of the invention.

In some applications, a first AP-1 modulator (e.g., targeted to c-fos) is used in combination with a second AP-1 modulator (e.g., targeted to c-jun) in order to modulate AP-1 molecules to a more extensive degree than cannot be achieved when one AP-1 modulator is used individually.

C. Delivery of Polynucleotides Encoding AP-1 Modulators

In some methods of the present invention, polynucleotides encoding AP-1 modulators of the present invention (e.g., those listed in Tables 1 and 2 or fragments thereof) are transfected into cells for therapeutic purposes in vitro and in vivo. These polynucleotides can be inserted into any of a number of well-known vectors for the transfection of target cells and organisms as described below. The nucleic acids are transfected into cells, ex vivo or in vivo, through the interaction of the vector and the target cell. The compositions are administered to a subject in an amount sufficient to elicit a therapeutic response in the subject.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

Delivery of the gene or genetic material into the cell is the first step in gene therapy treatment of disease. A large number of delivery methods are well known to those of skill in the art. Preferably, the polynucleotides are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In particular, a number of viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048-305 (1995); Kohn et al., *Nat. Med.* 1:1017-102 (1995); Malech et al., *Proc. Natl. Acad. Sci. U.S.A.* 94:22 12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors (Ellem et al., *Immunol Immunother.* 44(1):10-20 (1997); Dranoff et al., *Hum. Gene Ther.* 1:111-2 (1997)).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual subject (e.g., lymphocytes, bone marrow aspirates, tissue biopsy) or universal donor hematopoietic stem cells, followed by reimplantation of the cells into a subject, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., subject). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from subjects).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

EXAMPLES

The following examples are offered to illustrate, but not to limit the present invention.

Example 1

Identification of Novel AP-1 Modulators

This Example describes identification of various AP-1 modulatory polypeptides that regulate expression of a reporter gene under the control of an AP-1 enhancer element (an AP-1 recognition sequence). This AP-1 transcription regulatory element is present in genes encoding AP-1 subunits as well as genes regulated by an AP-1 transcription factor (AP-1 responsive genes).

The study employs an addressable library of more than 20,000 cDNAs (approximately 14,000 distinct genes) in the interrogation of the AP-1 signal transduction pathway. This platform is referred to as GFAcT (Genome Functionalization through Arrayed cDNA Transduction) analysis. Briefly, sequence annotated cDNAs were arrayed in 384-well plate format such that each well contained a single addressable gene. In a semi-automated process, the cDNAs were incubated with a non-liposomal transfection reagent (Fugene, Roche Applied Science, Indianapolis, Ind.) and a AP1 (PMA)-luciferase reporter vector (Clontech, Palo Alto, Calif.). This vector contains six tandem copies of an AP-1 enhancer element (TGACTAA) and a minimal promoter derived from Herpes simplex virus thymidine kinase (HSV-TK) promoter.

HEK 293 (human embryonic cell line) cells (Graham et al., Cold Spring Harbor Symp. Quant. Biol., 39:637-650, 1975) were then introduced into each well to complete the transfection procedure. After 2 days of incubation at 37 C, 5% $CO_2$, equal volumes of Bright-glo reagent (Promega, Madison, Wis.) was added to each well and relative luminescence was quantitated using an Acquest (LJL Biosystems, Sunnyvale, Calif.) plate reader.

After executing the assay in duplicate, plate data were normalized to a mean value and compared across the library (20,000 wells). cDNAs with mean activity values >2-3 standard deviations from the whole experimental mean we selected from the library, and were amplified and isolated utilizing commercially available DNA isolation reagents (Qiagen, Germany). These samples were reconfirmed utilizing the methods outlined above. The analysis detected a number of cDNAs which increased AP-1 reporter gene activities to a level greater than about 3 standard deviations from their respective experimental means (examples shown in Tables 1 and 2).

Example 2

Characterization of the Novel AP-1 Modulators

To evaluate the specificity of gene activities elucidated through the above GFAcT analysis, 15-30 of the most potent AP-1 modulators were cross-profiled for activities in modulating other pathways such as p53 function and erythropoietin gene transcription. The majority of the identified cDNAs showed preferential activation of a single reporter, indicating that this strategy uncovered distinct pathway modulators. In addition to identifying the gene activities, the study also, as expected, identified modulators that were known to be functionally associated with AP-1 pathway. For instance, c-FOS, c-JUN, GADD45, TRAF6, ERB-B-2, FOSL1, ATF3, MAP3K11, and were among the top 0.5% of activators in the AP-1 screen.

Through a pathway mapping strategy, the novel AP-1 modulators were categorized into two primary arms of AP-1 signaling: growth and proliferation, or stress and immune response. Specifically, the analysis profiled relative activities of the AP-1 modulators upon reporter genes responsive to growth and proliferation signals (serum response element (SRE), NFATc response elements (NFAT), and PMA response elements (AP-1 (PMA)), and also those that preferentially monitor inflammation, interferon, or stress stimuli (CREB response elements (CRE), interferon response elements (ISRE) and AP-1 response elements (AP-1)). Although all of the interrogated genes were identified through their abilities to modulate AP-1 (PMA) dependent reporter gene transcription to some level, this pathway mapping strategy enabled the further classification of novel AP-1 inducers based on comparative activation of related reporter constructs. In particular, hierarchical cluster analysis resulted in the co-segregation of reporter activities in relation to specific facets of AP-1 signaling (FIG. 1A). This distinguishes those encoded proteins likely involved with genotoxic stress and (pro-inflammatory) cytokine signaling (ISRE, AP-1, CRE), from, conversely, those affiliated with growth factor and serum response (SRE, AP-1(PMA), NFAT).

The study further investigated the mechanism of action of the subset of genes which were expected to regulate growth, proliferation and general AP-1 response pathways. Consistent with their postulated roles, transfection of most cDNAs from these predicted subsets resulted in the coordinate induction of c-FOS and/or c-JUN protein levels, as demonstrated by western blot analysis (FIG. 1B). However, expression of a few encoded proteins in this grouping, such as TYRO3, P2RY2, and UBB, did not result in detectable elevated levels of the prototypic AP-1 transcription factors, which may indicate that they modulate AP-1 activity through alternate family members, or through as yet unknown mechanisms. These results indicate that significant number the novel encoded proteins identified through GFAcT analysis are likely bonafide modulators of endogenous AP-1 activity. Intriguingly, analysis of mRNA distribution levels in human tissues revealed an coincident expression of predicted growth-associated AP-1 modulators and canonical AP-1 transcription factors which was largely restricted to cells of lymphoid origin (FIG. 1C), suggesting a functional alignment between these molecules in proliferating cell types.

To refine the mode of action by which the novel growth regulatory proteins are modulating the AP-1 pathway, their relative inductive activities were examined in the presence of small inhibitor RNA (siRNA) molecules directed against known components of AP-1 signaling. AP-1(PMA) reporter gene activities of pairwise cDNA (novel activators) and siRNA (AP-1 pathway members) transfections were normalized to appropriate controls and analyzed through single-linkage hierarchical clustering (FIG. 2A). For comparison, effects of the inhibitory RNAs upon PMA-induced AP-1 activity are also shown. siRNAs encoding PI-3 kinase (PIK3R3, PIK3CD), PKC (PKCD, PRKACA, DGKI, MEKK2), and RAS (SRC, RAF) pathway members were most proficient in abrogating the AP-1 induction by the bulk of the identified growth regulators. This demarcates a majority of identified AP-1 activators as functioning upstream of these proteins, and suggests that they regulate AP-1 activity through modulation of PI-3 Kinase, PKC, and/or RAS pathways. For example, the results indicate that the activity of BLK upon the AP-1 reporter gene was extinguished by siRNAs coding for ERK pathway effectors DGKI, MEKK1, SRC, RAF1 and PIK3R3, but not by siRNAs directed against JNK-related pathway molecules MAP3K7, MAPK9, and MAP4K4. These observed activities are consistent with reports that these and related family members are important for AP-1 response to environmental growth stimuli.

A notable exception in this characterization was seen by significant inhibitory activity of MAP4K1 (mitogen-activated protein kinase kinase kinase kinase 1) siRNA across the tested AP-1 activators, including upon PMA mediated AP-1 response. MAP4K1 has previously been demonstrated to meditate the stress and pro-inflammatory cytokine response JNK/SAPK kinase signaling cascade. These data may indicate a previously unappreciated role of this tyrosine kinase in mitogenic signaling. In sum, this genetic complementation strategy allowed for the identification of AP-1 pathway components required for the inductive activities of novel modulators, and further defined the junction at which these molecules intersect the AP-1 signaling cascade.

The roles of the predicted growth-associated AP-1 modulators in mitogenic response were also examined. Utilizing DNA expression plasmids encoding short hairpin RNAs (shRNA) directed against a subset of eight growth-related pathway activators, the inhibition of PMA induced AP-1 activity through reporter gene analysis was screened. Based upon their potent antagonism of PMA-induced reporter activity, shRNAs encoding sequences homologous to the B-lymphocyte kinase (BLK) and transitional epithelia response (TERE1) genes were selected for further characterization. Through western blot analysis, it was demonstrated that transfection of these shRNAs into PMA-stimulated cells resulted in a significant decrease in c-FOS induction in response to phorbol ester (FIG. 2B). These results reveal that these encoded proteins play critical roles in the AP-1 regulation by mitogenic stimuli in a human embryonic kidney cell line.

Analysis was performed to further elucidate the signaling mechanisms underlying the activities of AP-1 growth modulators required for undiminished c-FOS activation in response to phorbol ester stimuli. To this end, multi-protein complexes associated with BLK and TERE1 were examined through Immunoprecipitation Mass Spectrometry (IPMS) analysis. Notably, the tyrosine kinase BLK immunoprecipitated with CDC37 (cell division cycle 37 homolog (*S. cerevisiae*)), a chaperone protein which has been shown to regulate a variety of growth signaling molecules, including the AP-1 modulators SRC and RAF-1. Furthermore, it was identified that ATP5B (ATP synthase) and PHGDH (phosphoglycerate dehydrogenase) are protein partners for transitional epithelia response protein (TERE1). These molecules function as enzymatic components of the ATP and serine biosynthesis pathways, respectively. TERE1 was known to be critical for mitogenic response. These data indicate that regulation of intracellular serine, serine derivatives (i.e. phosphatidylserine, diacylglycerol), and/or ATP levels by TERE1-interacting proteins may be significant components of AP-1 signaling.

Given the role of AP-1 related proteins in proliferation and cancer-related phenotypes, the present inventors alternatively assessed the ability of these molecules to impart a growth advantage to mammalian cells. Proliferative control in primary chicken embryonic fibroblasts (CEFs) is particularly susceptible to modulation by AP-1 effectors, consistent with the avian retroviral origin of many AP-1 regulatory molecules. Growth analysis of CEFs ectopically expressing a subset of putative AP-1 growth regulatory genes demonstrates that these molecules can increase rates of proliferation and/or saturation densities in this primary cell type (FIG. 3A).

The oncogenic potential of these genes was interrogated in fibroblast transformation assays. Previous reports have shown that expression of TYRO3 can mediate foci formation in an immortalized cell type (RAT1 fibroblasts), and an activated mutant of BLK has also been previously demonstrated to possess oncogenic activities (Malek et al., Proc Natl Acad Sci USA 95, 7351-6, 1998). The present inventors discovered that forced expression of wild-type BLK resulted in loss of contact inhibition in CEFs as demonstrated by formation of foci (FIG. 3C), and that ectopic TYRO3 activity was sufficient to promote anchorage independent growth in a primary cell type (FIG. 3B). Finally, infection of CEFs with retroviruses encoding Centaurin-alpha 1 (CENTA1) and the hypothetical protein KIAA1847, which was designated TIAP (Tudor-domain containing Inducer of AP-1) by the present inventors, also resulted in a phenotype consistent with cellular transformation (FIG. 3B). Colonies derived from ectopic expression of these genes displayed a distinct diffuse morphology as compared with those formed by CEFs expressing c-JUN or TYRO3, but still maintained anchorage independent growth characteristics. These results confirm the in vivo proliferative activities of several of the growth associated AP-1 activators identified through GFAcT analysis.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, ATCC deposits, patents and patent applications cited herein are hereby expressly incorporated by reference in their entirety and for all purposes as if each is individually so denoted.

We claim:

1. A method for identifying an agent that modulates activity of activator protein 1 (AP-1), the method comprising:
    (a) assaying a biological activity of an AP-1-modulatory polypeptide encoded by a polynucleotide that encodes Homo sapiens B lymohoid tyrosine kinase (BLK), or a biologically active fragment of said polypeptide, in the presence of a test agent to identify one or more modulating agents that modulate the biological activity of the polypeptide; and
    (b) testing one or more of the modulating agents for ability to modulate the AP-1 transcription factor activity.

2. The method of claim 1, wherein (b) comprises testing the modulating agents for ability to modulate the AP-1 transcription factor in regulating expression of an AP-1 responsive gene.

3. The method of claim 1, wherein (b) comprises testing the modulating agents for ability to modulate cellular level of the AP-1 transcription factor or a subunit of the AP-1 transcription factor.

4. The method of claim 3, wherein the AP-1 subunit is selected from the group consisting of c-Fos, FosB, Fra-1, Fra-2, c-Jun, JunB and JunD.

5. The method of claim 1, wherein the AP-1-modulatory polypeptide is a kinase and the biological activity is phosphorylation of a second polypeptide.

6. The method of claim 1, wherein the test agent modulates the cellular level of the AP-1-modulatory polypeptide.

7. The method of claim 1, wherein the assaying of the biological activity of the AP-1-modulatory polypeptide occurs in a cell.

8. The method of claim 7, wherein the AP-1-modulatory polypeptide is expressed from a polynucleotide that encodes the AP-1-modulatory polypeptide and that has been introduced into the cell.

9. The method of claim 1, wherein the AP-1 transcription factor activity is inducing expression of a second polynucleotide that is operably linked to an AP-1 response element.

10. The method of claim 9, wherein the second polynucleotide encodes a reporter polypeptide.

11. The method of claim 9, wherein the testing for ability to modulate the AP-1 transcription factor activity comprises:
    providing a cell or cell lysate that comprises the second polynucleotide that is operably linked to the AP-1 response element;
    contacting the cell or cell lysate with the test agent; and
    detecting an increase or decrease in expression of the second polynucleotide in the presence of the test agent compared to expression of the second polynucleotide in the absence of the test agent.

12. The method of claim 1, wherein the testing for ability to modulate the AP-1 transcription factor activity comprises contacting a cell or cell lysate with the test agent and determining cellular level of the AP-1 transcription factor or a subunit of the AP-1 transcription factor.

13. The method of claim 12, wherein the AP-1 transcription factor is a Jun/Fos heterodimer.

14. The method of claim 12, wherein the subunit of the AP-1 transcription factor is selected from the group consisting of c-Fos, FosB, Fra-1, Fra-2, c-Jun, JunB and JunD.

15. The method of claim 1, wherein the testing for ability to modulate the AP-1 transcription factor activity comprises contacting a cell or cell lysate with the test agent and determining ability of the AP-1 transcription factor to bind to a second polynucleotide that comprises an AP-1 response element in the cell or cell lysate.

16. The method of claim 15, wherein the AP-1 transcription factor is a Jun/Fos heterodimer.

17. A method for identifying an agent that modulates expression of an AP-1 responsive gene, the method comprising:
    (a) contacting a test agent with an AP-1-modulatory polypeptide encoded by a polynucleotide that encodes Homo sapiens B lymphoid tyrosine kinase (BLK);
    (b) detecting a change in an activity of said AP-1-modulatory polypeptide relative to the activity in the absence of the test agent; and
    (c) detecting a change of expression level of the AP-1 responsive gene in the presence of the test agent identified in (b) relative to expression level of the AP-1 responsive gene in the absence of the test agent; thereby identifying the test agent as a modulator of expression of the AP-1 responsive gene.

18. The method of claim 17, wherein (a) and (b) are performed in a cell.

* * * * *